(12) United States Patent
Schwarz

(10) Patent No.: US 11,896,299 B2
(45) Date of Patent: Feb. 13, 2024

(54) MODULAR TREATMENT DEVICE

(71) Applicant: BTL HEALTHCARE TECHNOLOGIES A.S., Prague (CZ)

(72) Inventor: Tomás Schwarz, Prague (CZ)

(73) Assignee: BTL HEALTHCARE TECHNOLOGIES A.S., Prague (CZ)

( * ) Notice: Subject to any disclaimer, the term of this patent is extended or adjusted under 35 U.S.C. 154(b) by 193 days.

(21) Appl. No.: 17/498,610

(22) Filed: Oct. 11, 2021

(65) Prior Publication Data

US 2022/0023652 A1   Jan. 27, 2022

Related U.S. Application Data

(63) Continuation of application No. 15/678,915, filed on Aug. 16, 2017, now Pat. No. 11,141,219.
(Continued)

(51) Int. Cl.
*A61B 18/18* (2006.01)
*A61F 13/64* (2006.01)
(Continued)

(52) U.S. Cl.
CPC .............. *A61B 18/18* (2013.01); *A61F 13/64* (2013.01); *A61F 13/66* (2013.01);
(Continued)

(58) Field of Classification Search
CPC .......... A61B 18/18; A61B 2018/00005; A61B 2018/00172; A61B 2018/00273; A61B 2018/00464; A61B 2018/00654; A61B 2018/00916; A61B 2018/00958; A61B 2018/00988; A61B 2018/00994;
(Continued)

(56) References Cited

U.S. PATENT DOCUMENTS 5,419,344 A   5/1995 Dewitt
5,755,753 A   5/1998 Knowlton
(Continued)

FOREIGN PATENT DOCUMENTS

BR   PI08125023      6/2015
CN   102711706 A    10/2012
(Continued)

OTHER PUBLICATIONS

Kocbach et al., A Simulation Approach to Optimizing Performance of Equipment for Thermostimulation of Muscle Tissue using COMSOL Multiphysics, Biophysics & Bioeng. Letters, 4(2), (2011) (26 pages).
(Continued)

*Primary Examiner* — Mark W. Bockelman
(74) *Attorney, Agent, or Firm* — Riverside Law LLP

(57) ABSTRACT

A method of treating tissue of a patient uses a device including a mother case, a belt, at least one treatment unit and at least two applicators. The treatment method may include attaching first and second applicators to the belt at a working distance to the patient's surface, and providing different treatment energy to the first applicator and the second applicator. A treatment pattern is created by the applicators providing the different treatment energies. The hardware pattern or positions of the applicators on the belt may be changed before and/or during the treatment. The hardware pattern may be based on selected treatment effect and body part.

32 Claims, 12 Drawing Sheets

Related U.S. Application Data

(60) Provisional application No. 62/375,796, filed on Aug. 16, 2016.

(51) Int. Cl.
*A61F 13/66* (2006.01)
*A61B 18/00* (2006.01)

(52) U.S. Cl.
CPC ............... *A61B 2018/00005* (2013.01); *A61B 2018/00172* (2013.01); *A61B 2018/00273* (2013.01); *A61B 2018/00464* (2013.01); *A61B 2018/00654* (2013.01); *A61B 2018/00916* (2013.01); *A61B 2018/00958* (2013.01); *A61B 2018/00988* (2013.01); *A61B 2018/00994* (2013.01)

(58) Field of Classification Search
CPC . A61B 18/14; A61B 2018/0047; A61F 13/64; A61F 13/66; A61F 7/02; A61F 2007/0022; A61F 2007/0027; A61F 2007/0031; A61F 2007/0034; A61F 2007/004; A61F 2007/0041; A61F 2007/0228; A61F 2007/029; A61N 2005/0626; A61N 2005/0645; A61N 1/0452; A61N 1/0484; A61N 1/328; A61N 1/40; A61N 2/002; A61N 5/0616; A61N 7/00; A61N 7/02; A61N 2007/0008; A61N 2007/0034
See application file for complete search history.

(56) References Cited

U.S. PATENT DOCUMENTS

| | | |
|---|---|---|
| 5,919,219 A | 7/1999 | Knowlton |
| 6,094,599 A | 7/2000 | Bingham |
| 6,246,905 B1 | 6/2001 | Mogul |
| 6,273,884 B1 | 8/2001 | Altshuler |
| 6,311,090 B1 | 10/2001 | Knowlton |
| 6,453,202 B1 | 9/2002 | Knowlton |
| 6,735,481 B1 | 5/2004 | Bingham |
| 6,920,883 B2 | 7/2005 | Bessette |
| 7,083,580 B2 | 8/2006 | Bernabei |
| 7,376,460 B2 | 5/2008 | Bernabei |
| 7,496,401 B2 | 2/2009 | Bernabei |
| 7,520,875 B2 | 4/2009 | Bernabei |
| 7,532,926 B2 | 5/2009 | Bernabei |
| 7,571,003 B2 | 8/2009 | Pozzato |
| 7,618,429 B2 | 11/2009 | Mulholland |
| 7,914,469 B2 | 3/2011 | Torbati |
| 7,945,321 B2 | 5/2011 | Bernabei |
| 7,953,500 B2 | 5/2011 | Bingham |
| 8,172,835 B2 | 5/2012 | Leyh |
| 8,454,591 B2 | 6/2013 | Leyh |
| 8,457,751 B2 | 6/2013 | Pozzato |
| 8,548,599 B2 | 10/2013 | Zarsky |
| 8,646,239 B2 | 2/2014 | Rulon |
| 8,700,176 B2 | 4/2014 | Azar |
| 8,725,270 B2 | 5/2014 | Towe |
| 9,061,128 B2 | 6/2015 | Hall |
| 9,168,096 B2 | 10/2015 | Kreindel |
| 9,265,690 B2 | 2/2016 | Kriksunov |
| 9,532,832 B2 | 1/2017 | Ron Edoute |
| 9,561,357 B2 | 2/2017 | Hall |
| 9,596,920 B2 | 3/2017 | Shalev |
| 9,782,324 B2 | 10/2017 | Crunick |
| 9,867,996 B2 | 1/2018 | Zarsky |
| 10,195,453 B2 | 2/2019 | Schwarz |
| 10,583,287 B2 | 3/2020 | Schwarz |
| 2002/0165590 A1 | 11/2002 | Crowe |
| 2003/0149451 A1 | 8/2003 | Chomenky |
| 2004/0093042 A1 | 5/2004 | Altshuler |
| 2004/0162583 A1 | 8/2004 | Bingham |
| 2004/0230226 A1 | 11/2004 | Bingham |
| 2006/0206103 A1 | 9/2006 | Altshuler |
| 2006/0271028 A1 | 11/2006 | Altshuler |
| 2007/0293911 A1 | 12/2007 | Crowe |
| 2009/0043293 A1 | 2/2009 | Pankratov |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0274329 A1 | 10/2010 | Bradley |
| 2011/0009737 A1 | 1/2011 | Manstein |
| 2011/0046523 A1 | 2/2011 | Altshuler |
| 2011/0172752 A1 | 7/2011 | Bingham |
| 2012/0046653 A1 | 2/2012 | Welches |
| 2012/0116271 A1 | 5/2012 | Caruso |
| 2012/0271206 A1 | 10/2012 | Shalev |
| 2012/0310311 A1 | 12/2012 | Elkah |
| 2013/0123629 A1 | 5/2013 | Rosenberg |
| 2013/0123764 A1 | 5/2013 | Zarsky |
| 2013/0123765 A1 | 5/2013 | Zarsky |
| 2013/0158634 A1 | 6/2013 | Ron Edoute |
| 2013/0238061 A1 | 9/2013 | Ron Edoute |
| 2014/0249609 A1 | 9/2014 | Zarsky |
| 2014/0276248 A1 | 9/2014 | Hall |
| 2015/0157873 A1 | 6/2015 | Sokolowski |
| 2016/0045755 A1 | 2/2016 | Chun |
| 2016/0106982 A1 | 4/2016 | Cakmak |
| 2016/0121112 A1 | 5/2016 | Azar |
| 2016/0158574 A1 | 6/2016 | Eckhouse |
| 2017/0050019 A1 | 2/2017 | Ron Edoute |
| 2017/0100585 A1 | 4/2017 | Hall |
| 2017/0143958 A1 | 5/2017 | Shalev |
| 2017/0239467 A1 | 8/2017 | Shalev |
| 2019/0000529 A1 | 1/2019 | Kothare |
| 2019/0134414 A1 | 5/2019 | Prouza |
| 2019/0151655 A1 | 5/2019 | Hall |
| 2019/0192219 A1 | 6/2019 | Kreindel |
| 2019/0314629 A1 | 10/2019 | Kreindel |
| 2019/0314638 A1 | 10/2019 | Kreindel |
| 2019/0350646 A1 | 11/2019 | Kreindel |
| 2020/0129759 A1 | 4/2020 | Schwarz |
| 2020/0237424 A1 | 7/2020 | Hunziker |
| 2020/0281642 A1 | 9/2020 | Kreindel |

FOREIGN PATENT DOCUMENTS

| | | |
|---|---|---|
| EP | 2461765 A1 | 6/2012 |
| EP | 2614807 A1 | 7/2013 |
| EP | 2501352 B1 | 7/2016 |
| EP | 3389532 A1 | 10/2018 |
| JP | 2013063285 A | 4/2013 |
| KR | 20120037011 A | 4/2012 |
| KR | 20130128391 A | 11/2013 |
| KR | 101941863 B1 | 1/2019 |
| WO | 0112089 A1 | 2/2001 |
| WO | 2004108211 A1 | 12/2004 |
| WO | 2008012827 A2 | 1/2008 |
| WO | 2009013729 A2 | 1/2009 |
| WO | 2009044400 A2 | 4/2009 |
| WO | 2011016019 A1 | 2/2011 |
| WO | 2011058565 A2 | 5/2011 |
| WO | 2011156495 A2 | 12/2011 |
| WO | 2012029065 A2 | 3/2012 |
| WO | 2013074576 A2 | 5/2013 |
| WO | 2014141229 A1 | 9/2014 |
| WO | 2014149021 A2 | 9/2014 |
| WO | 2014151431 A2 | 9/2014 |
| WO | 2017103923 A1 | 6/2017 |
| WO | 2020002801 A1 | 1/2020 |
| WO | 2020035852 A2 | 2/2020 |

OTHER PUBLICATIONS

Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Notice of Allowance dated Aug. 23, 2021 for U.S. Appl. No. 15/678,915 (pp. 1-5).

(56) References Cited

OTHER PUBLICATIONS

Office Action dated Dec. 24, 2020 for U.S. Appl. No. 15/678,915 (pp. 1-6).
Office Action dated Jul. 10, 2020 for U.S. Appl. No. 15/678,915 (pp. 1-9).
Office Action dated Oct. 7, 2019 for U.S. Appl. No. 15/678,915 (pp. 1-8).
Pollogen, Maximus Non-invasive body shaping System, User Manual, dated May 1, 2012, 44 pages.
Pollogen, TriFractional FAQs, User Manual, dated Aug. 2011, 4 pages.
TriLipo MED Procedure, http://download.lifvation.com/Maximus_TriLipoMED_Intro.pdf, Apr. 2013 (66 pages).
Venus Swan, Experience the Difference, Venus Concept, Delivering the Promise, 2 pages.
Wanitphakdeedecha et al., "Treatment of abdominal cellulite and circumference reduction with radiofrequency and dynamic muscle activation" Article in Journal of Cosmetic and Laser Therapy, dated Apr. 6, 2015, 7 pages.

MODULAR TREATMENT DEVICE

CROSS-REFERENCE TO RELATED APPLICATION(S)

This application is a continuation of U.S. patent application Ser. No. 15/678,915, filed Aug. 16, 2017, now pending, which claims priority to and benefit of U.S. Provisional Application No. 62/375,796 filed Aug. 16, 2016, both of which are incorporated herein by reference in their entireties.

TECHNICAL FIELD

The field of the invention is an apparatus and methods with a high degree of modularity directed to a self-operated device for aesthetic treatment using a combination of one or more treatment applicators that may provide one or more types of treatment energy to the patient's tissue.

BACKGROUND

Human skin is tissue which is commonly treated in order to improve its visual appearance. Skin is composed of three basic elements: the epidermis, the dermis and the hypodermis or so called subcutis. The outer and also thinnest layer of skin is the epidermis. Epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of the fat cells. The fat cells create lobules which are bounded by connective tissue, fibrous septa (retinaculum cutis).

Another part of adipose tissue located in peritoneal cavity is known as abdominal obesity. The visceral fat layer forming visceral white adipose tissue (VWAT) is located between the parietal peritoneum and the visceral peritoneum, closely below muscle fibers adjoining the hypodermis layer.

Excess adipose tissue in the subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been linked to various cardiovascular diseases and diabetes.

The undesirable skin appearance (e.g. topographic skin appearance) may also be caused by changes in the dermal or sub-dermal layer of the skin, especially by excessive numbers or volume of fat cells, weakening of fibrous septas, loss of elasticity, collagen structural or volume changes and/or limited lymph flow, which may result in accumulation of toxins.

Pigment inhomogeneity caused by structural changes in epidermis, by pigment granules contraction or expansion, pigment migration in the skin may also lead to low self-confidence of people with this skin condition.

Current devices for aesthetic use have limited modularity. The operator have to use two or more different applicators and provide separate treatment one by one in order to achieve the most desirable results which is time consuming, expensive and therefore some patients may not be able to afford it. No device and/or method in the current state of art are able to provide large scale of treatment therapies during one treatment session and with a large treated area and large range of hardware modularity. Current state of art apparatus are not able to change hardware patterns during one session, cannot connect another device during treatment and cannot operate without operator. No device of the current state of art can resist against outdating like presented modular device and method of use. Self-operated devices have several benefits e.g.: fast reaction on changed therapy condition, preventing human mistakes, time saving, saving data from previous treatment and learn from them etc. Multiple therapies also improve the effect and safety of the treatment. Operator guiding treatment applicators are not able to simultaneously provide multiple different therapies across the large patient surface. There is a need for apparatus and methods that allow an operator to choose several treatment types that can work treat with minimal attendance of user.

Current state of art apparatuses provide complex treatment are very expensive what is also the reason of high price of one treatment session. Price of current state of art apparatus may be also the reason why a purchaser hesitates between cheap lower quality apparatus and apparatus of high quality but very expensive.

Solution of reducing initial cost of high quality apparatus may be renting of the device adapted to these needs.

SUMMARY

Described herein is a device and method of its use for aesthetic treatment with multiple types of treatment energy that may be delivered into various body parts includes e.g.: bra fat area, buttocks, saddlebags, love handles, abdomen, hips, thighs, arms, limb, back, cervical body part, also muscle or muscle group of mentioned body parts and/or any other tissue. Treatment energy may be delivered to the tissue of the patient in sequential and/or simultaneous manner. Different aesthetic skin and/or body treatment effect are provided, e.g.: wrinkle reduction, skin tightening, skin rejuvenation, skin viability, removing of unwanted hair, removing of pigment and/or other skin imperfections (e.g.: atopic eczema, psoriasis, erysipelas, dermatomyositis, lupus, hives, acne, skin veins and/or scars, collagen inhomogeneity, etc.), removing of cellulite, body shaping, muscle stimulation, fat removing, anti-edema and anti-erythema effect, improving blood and lymph circulation, and/or accelerating body metabolism.

In one aspect the device is designed as a mother case with one or more treatment units ensuring control and/or generation of treatment energy, one or more applicators directing the treatment energy into the body and a belt for displacing the applicators into the pattern in proximity of the patient's body. The mother case may be modularly modified by adding and/or removing one or more part of the device (e.g.: applicators, treatment units) before and/or during the treatment.

Treatment applicators may provide different types of treatment energy e.g.: radio-frequency therapy (RF therapy), plasma therapy, ultra-sound therapy, acoustic wave, shock wave therapy, light (coherent, non-coherent) therapy, heating, cooling, electro-therapy, therapy by generated magnetic field (include muscle stimulation), positive or negative pressure therapy, vibration therapy and/or massage therapy. Treatments may be performed completely without manual operation or even attendance of the operator and/or treatment procedures may by modified during the treatment. One or more treatment applicators may communicate with each other and/or with one or more control units via cables, wireless and/or via connection through the belt. The communication may provide information about location and/or type of the applicator, treatment protocol, treatment parameters and other information.

The invention is characterized by method and modular apparatus with a belt and/or arrangement of the applicators enabling multiple treatment procedures and/or therapies at the same time. This improves the effectivity of the treatment and/or reduces the time needed for the treatment and improves homogeneity and safety. The combination also provides treatment of same or different tissue structures which may result in synergic improvement of treatment result.

The belt is designed to fit any type and size of treated patient body area. In one preferred embodiment the belt is created by supporting matrix with attached applicators in arbitrary 2D or 3D hardware pattern. Belt is in touch with patient's body surface and matches the curvature of patient's body. The belt is designed in order to fit one or more applicators providing at least two different types of treatment energy. Size of the belt may be variable by stretching and/or by plugging and/or removing of one or more parts of the supporting matrix part and/or applicators. Supporting matrix enable to placed applicator at working distance at arbitrary location on patient's body.

In another embodiment the belt may be considered as a block of at least two treatment applicators attached in optimal working distance to the patient's body.

The modular apparatus may operate without any manual operation or even without and/or with slight attendance of an operator which saves time and money. One operator may supervise more than one treated patient. The apparatus may prevent mistakes during the treatment caused by human factors. The apparatus may also have a better response to changed conditions of the treatment and/or may provide more homogenous and precise treatment which improves results and safety of the treatment. With the apparatus controlled by a computer, responses to changed conditions are improved because the apparatus can react on e.g.: moving of the patient or some structural changes in the soft tissue, etc.; faster than 0.1 s, and human response is at least 0.5 s.

The modular apparatus with a belt provides an easy way to change treatment procedures and parameters before and/or during the treatment. Modular system provides various patterns of treatment based on treatment applicators connected to the belt. Modular system may provide to the operator suggestion of applicator displacement in the belt system based on the treatment effect, age, sex and or other parameters. Such modularity enables personalized treatment for each patient.

The present invention solves the problem of device obsolescence due to large scale modularity. The device and method enables hardware and/or treatment pattern changes. The belt may or may not contain supporting matrix. The belt may be flexible, whole or partly elastic and may be adapted to patient surface of arbitrary size and shape. This characteristic helps to provide optimal energy transfer from an applicator to the patient soft tissue. Improved contact with the patient skin or surface may decrease or prevent an edge effect, backscattering of delivered energy and/or provides better conditions for collecting feedback information. Supporting matrix may also be connected to upper side of the applicator, keep one or more applicators in touch with the patient surface, and not be in touch with the patient.

In another embodiment the device may comprise several treatment units. Each treatment unit ensures control and/or generation of treatment energy for at least one treatment applicator. The separation of treatment units decrease price of the device and customer may add (purchase or rent) additional treatment units according to his needs and improve the functionality of the device. In alternative embodiment the treatment units may be plugged into a mother case. Modularity also prevent presented device against obsolete.

One treatment unit may be specialized for providing particular treatment energies and particular treatment effects. In order to achieve all the necessary scale of treatment effects another treatment unit may be specialized for providing different treatment energies and different treatment effects. The treatment units may include different components and/or different technological level of components which may allow just the therapies the operator needs.

In one embodiment the device may contain a master unit and one or more therapy generators.

In still another embodiment one or more of the applicators may include its own control unit which may cooperate with one or more control units of the respective treatment unit and/or with a central control unit. The device also may include billing and rental system counting renting of the device, treatment units and/or applicators and pricing the user by the treatment procedure, length of rent. Customer may improve its device by renting only the modules necessary for his needs, allowing for reductions in cost, that improves accessibility to doctors and clinics.

In another embodiment the presented method and device may include an emulator software and/or hardware parts that allow interconnecting arbitrary external device, treatment unit, applicator in order to communicate and participate on the pattern treatment. The device may include communication system that enables communication between external devices e.g. PC, laptop, mobile and others.

According to one embodiment the belt may be wearable and the mother case with treatment unit/s may be part of the wearable belt.

DETAILED DESCRIPTION

Glossary

Tissue includes skin, muscles, fat, fibrous tissue, nervous tissue (e.g. neurons, motor neuron, and neuromuscular junction), connective tissue, bone tissue and other human or animal tissue Patient is a biological material, mainly a human or an animal body.

Figure 1:
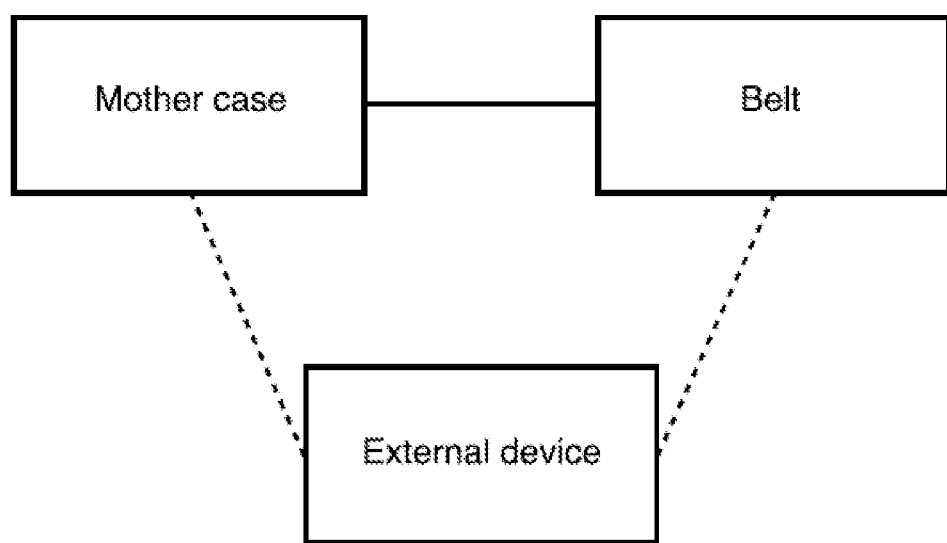
FIG. 1 is schematic diagram representing main segments of the device and communication between them.

FIG. 1 is schematic diagram representing main segments of the device and communication between them. The device is designed as a mother case with one or more treatment units ensuring control and/or generation of treatment energy, and a belt with one or more applicators directing the treatment energy into the body. The belt displaces the applicators into the pattern in proximity of the patient's body. The mother case may be alternatively connected with an external device connected with the belt by own separated applicator. According another embodiment the mother case may be substituted by one or more treatment units and/or external device(s).

Figure 2:
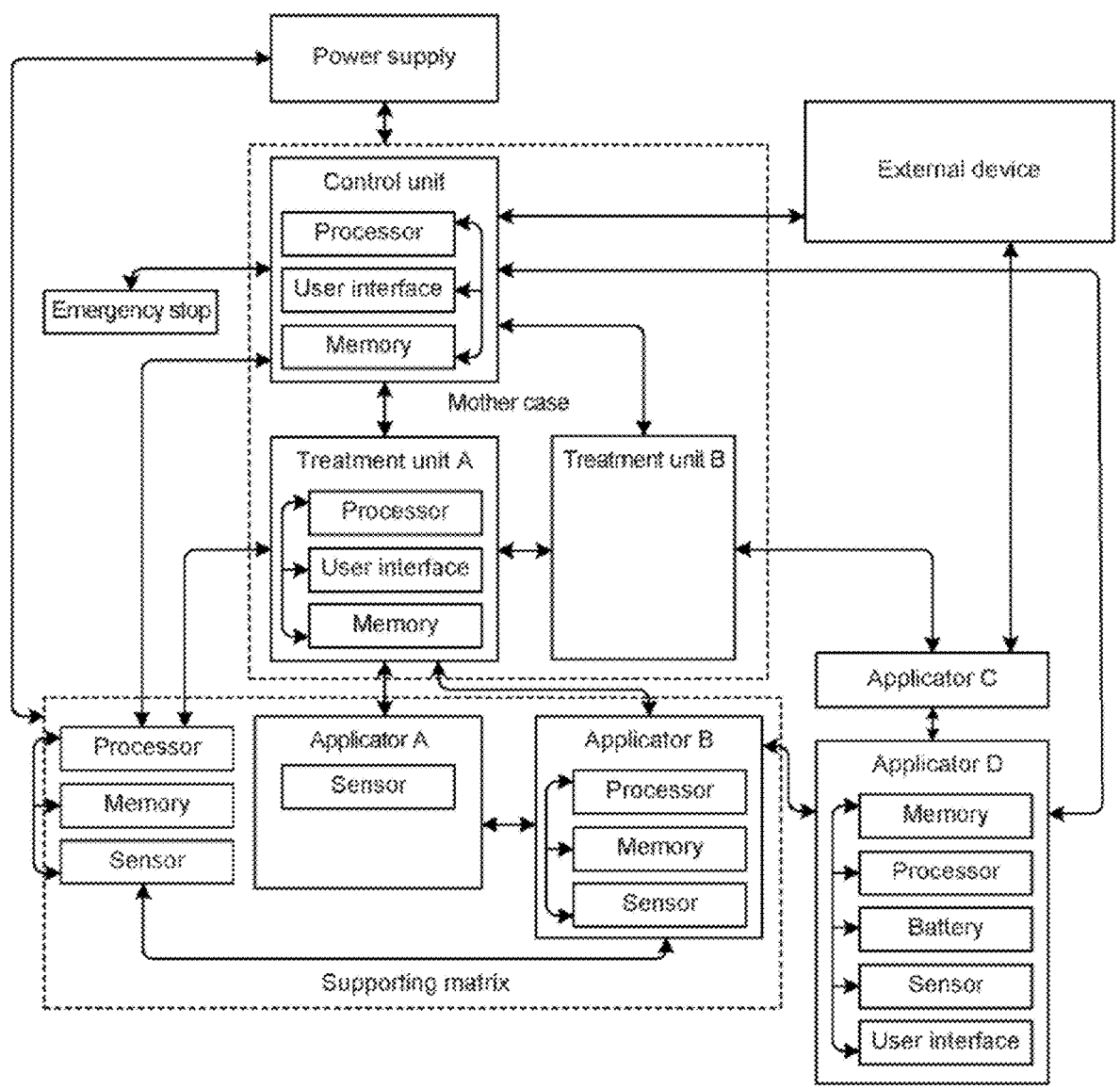
FIG. 2 is a schematic diagram of one possible embodiment of the device and communication between its individual parts.

FIG. 2 is a schematic diagram of one possible embodiment of the device and communication between its individual parts. The device is powered by a power supply. The power supply may be electricity from external source e.g. electrical power grid; and/or from batteries included in any part of the device. Part of the device such as: a mother case, a control unit, belt (e.g. supporting matrix), one or more treatment units, one or more external devices and/or one or more applicators may include direct connection with the power supply and/or may include batteries. Any part of the device may be powered trough connection between other part(s) of the device. For example applicator may be powered by treatment unit, by supporting matrix, by mother case and/or other part of the device. Also one or more treatment units may be powered e.g. by mother case, external device, supporting matrix and/or directly by connection to power grid.

According one of possible embodiment illustrated in the FIG. 2 Supporting matrix may be powered by the power supply and then be used as power supply for several applicator(s) attached to the supporting matrix.

The mother case described in detail later in this document may include the control unit and/or one or more treatment units which may have different specification. Treatment units and applicators may be specialized to provide specific type(s) of treatment therapies by one or more treatment energies and/or may cause one or more treatment effect(s). The control unit may process treatment parameters, protocols and/or other information based on binary code.

The treatment unit may include hardware and/or software components that may modify incoming electric signal and/or communication signal to the treatment unit. Such modified electric signal and/or communication signal may be provided into the applicator(s), supporting matrix, external device and/or other part of the device in order to provide treatment energy by one or more specific treatment energy sources. The applicator(s) may also modify delivered electric signal and/or process communication information.

As illustrated in the FIG. 2, some parts of the device e.g. treatment unit B; may not include a processor, a memory, a sensor, a battery, an user interface and/or other. The missing features may be substituted by other part of the device that includes such feature.

As illustrated in the FIG. 2, the device may include the processor and may process information individually and/or in cooperation with other parts including the processor. In one embodiment any processor may call stored information from any memory of one or more part of the device.

The belt may be designed as supporting matrix with attached applicators to optimal working distance to patient's body. Optimal working distance may be different for different types of the applicators and/or different treatment energy sources. For example optimal working distance for muscle stimulating electrode may be direct contact with the patient's surface and on the other hand optimal working distance for RF electrode providing heating of patient's adipose tissue may be several millimeters. Optimal working distance of the applicator(s) and/or treatment energy source(s) may be set by design of the applicator(s), supporting matrix, spacing object and/or fastening member. The applicator(s) may be in contact with patient's surface and/or in proximity to patient's surface spaced by patient's surface by any material and/or air gap.

According another embodiment the belt may be created by hardware pattern of treatment energy sources where at least two of them provides different type of treatment energy. Hardware pattern of treatment energy sources may be predefined from the factory and/or according another embodiment may be rearranged according individual needs of the patient. Belt according such embodiment may be wearable during the day, wherein the mother case (e.g. frame with GUI) with treatment unit/s may be incorporated inside the wearable belt. According such embodiment patient may choose some of predefined treatment protocols from list of treatment protocols. Protocols may be based on one or more wanted treatment effect(s), treated body part(s), hardware pattern of the belt and/or other features. The belt according such embodiment may be remote controlled, by patient and/or by other educated competent user. The belt according such embodiment may be wireless and may be powered by batteries. According still the same embodiment the belt may be in wireless communication with the external device.

The support matrix may include the processor, the memory and/or the sensor. for monitoring and/or evaluating at least one treatment parameter and/or may send feedback information to any connected part of the device e.g.: the control unit, the treatment unit(s), the external device(s) and/or the Applicator(s). Some of the applicators may not be attached to the supporting matrix but may communicate with the supporting matrix. Applicators may also communicate between each other.

Any part of the device may include manual and/or a virtual emergency stop button. The emergency stop button may immediately stop any and/or all of delivering treatment energies to the patient's body.

Figure 3:
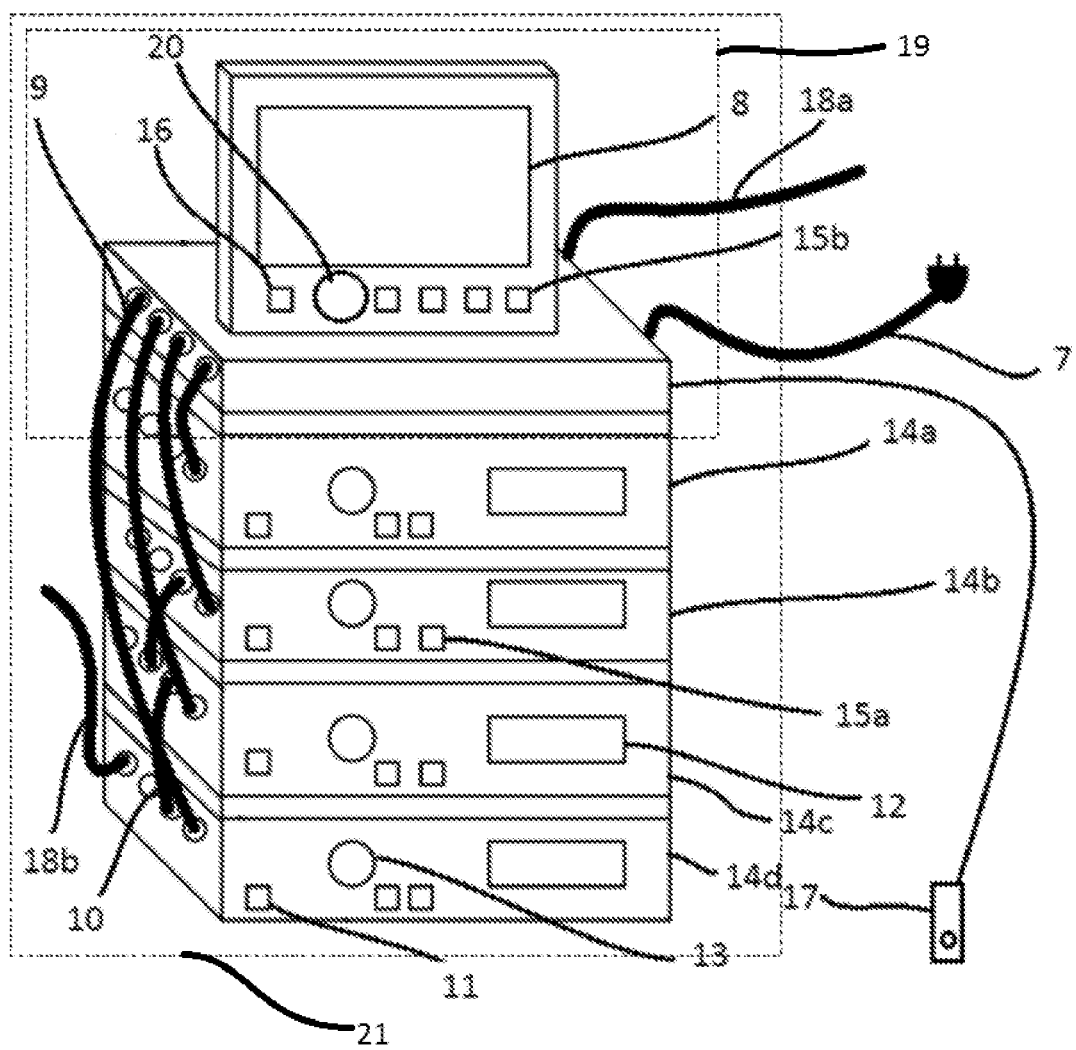
FIG. 3 illustrates mother case with control unit and multiple treatment units.

In FIG. 3 is depicted mother case with control unit and multiple treatment units. The mother case may include the control unit 19 of the mother case 21 and one or more treatment units (14a-14d) that may be added according to treatment needs. Individual treatment units (14a-14d) may be designed to provide specific one or more treatment effects and/or one or more treatment energies, e.g. RF waves, electric current, magnetic field, acoustic waves, shock wave, ultrasound waves, light waves, applied lower/higher pressure, friction, plasma, heat, cool and/or other. The control unit 19 may include a user interface in a form of a touch display 8, several buttons 15a, 15b, a circle control element 20, and a switch button 16. Also individual treatment units (14a-14d) may include its own user interface that may communicate with an external device, between each other and/or with the control unit 19. The control unit 19 may include the processor and the memory in order to guide treatment process, store information about treatment including feedback information consumption of individual parts of the device and/or may also include billing system. The mother case 21, the control unit 19, the treatment units (14a-14d), the external device or server may a include black box (e.g. memory) storing data of the treatment history, communication between individual parts of the device, data for billing system and/or may store many other data.

The mother case 21 may include slots for the treatment units (14a-14d). The treatment unit may be fixed in the right position by specific type of fastening mechanism that is described below. A fastening mechanism used to fix and/or connect treatment units (14a-14d) to the mother case 21 may by different for different type of Treatment units (14a-14d) and/or may be universal for all of the treatment units (14a-14d)

Recognition of the treatment unit may be trough specific impedance of connected part, RFID tag, pins, sequence of specific electrical and/or electromagnetic pulses, measuring of magnetic field in/near the connection that may be specific for individual type of the treatment unit, software recognition, specific binary ID, by recognition of connected optical signal from the treatment unit and/or trough other one or more mechanisms. Described system for recognition of the treatment unit may also be used for recognition of individual applicator(s) and/or external device(s). Connection/communication between mother case, treatment unit(s), control unit, applicator(s), supporting matrix and/or external device(s) may be wirelessly, by cable 9, by contact pins, one or more magnets, one or more conductive parts and/or by chassis.

Treatment units (14a-14d) may guide treatment provided by one or more applicators independently on the control unit 19 or in cooperation with control unit 19. Some of treatment units (14a-14d) may not include processor, memory and/or user interface and may be just means of connection specific one or more applicators and their management. Treatment units (14a-14d) may be also interconnected. Treatment units may be interconnected between each other.

The respective treatment units may be connected and fixed in the right slot position of the mother case in plug and play regime. The treatment unit may include energy socket or pin connectors to be plugged with mother case. The at least one connector may ensure the energy charge, data communication and/or fluid communication (e.g. in case of cooling, or use of plasma) with the mother case. Alternatively the data communication between mother case and treatment unit may be wirelessly, by cable, one or more magnets. Recognition of the treatment unit may be trough specific impedance, RFID tag, pins, sequence of specific electrical and/or electromagnetic pulses measuring of magnetic field that may be specific for individual type of the treatment unit, software recognition and/or trough other one or more mechanisms. The treatment unit may further include at least one socket/pin for the applicator. The treatment units and also the slots for the treatment units in the mother case may include electromagnetic shielding, vibration shielding, thermal shielding and electric insulation. The plug and play modular device for individual connecting of treatment units provides a large scale of modularity which enables to decrease the cost for the device, occupied space and increase optionality in order to fit all users.

Applicators directing the treatment energy into the body may be connected and/or communicate between each other, with Supporting matrix, one or more treatment units, the control unit 19 and/or to the external device. The applicator may include one or more: treatment energy sources, processors, sensors and/or the memory.

The external device may be used to provide and/or control at least part of the treatment. The external device may guide and/or communicate with at least one: applicator, treatment unit and/or control unit. The external device may be any treatment device able to provide treatment energy source. The external device may be also a device (e.g. computer, tablet, smartphone) that is not able to provide treatment energy source but communicate with the device and is able to monitor treatment and/or adjust treatment parameters.

Communication between individual parts of the device may be based on peer-to-peer and/or master-slave communication. During peer-to-peer communication the individual parts of the device have the same priority of its commands and communicate directly between each other. Peer-to-peer communication may be used during initial recognition of connected individual parts of the device. Peer-to-peer communication may be also used between some parts of the device during a treatment. Before and/or during each treatment is used master-slave communication at least for short time.

During master-slave communication one part of the device, provides commands with highest priority. Part of the device that provides commands with the highest priority at that time is called master unit.

According one embodiment a master unit may be determined by choice of user before and/or during the treatment. User may determine master unit e.g.: control unit, one of treatment unit(s) or external device(s) (e.g. laptop, tablet).

According another embodiment the master unit may be determined automatically based on predetermined priority value of connected parts of the device. For example a treatment unit A may be the master unit but after connection of a treatment unit B or the external device to the mother case, the treatment unit B or the external device become master unit.

At least two parts of the device and/or features may communicate to each other and/or to external device by optical cable, conductive cable, by other conductive connection and/or wirelessly. Wireless communication may be provided by internet network, local network, RF waves, acoustic waves, optical waves, 3G, 4G, LTE network, Bluetooth and/or other.

FIGS. 4-7 illustrates several of possible master-slave communication schemes. According schemas in the FIGS. 4-7 a therapy generator generates modified electrical signal in order to provide it to treatment energy source and provide treatment effect. Therapy generators may be e.g. treatment unit, applicator(s).

The master unit according previous definition includes processor and provides commands with highest priority.

Box A security according in FIGS. 4-7 may symbolize coding of the information used in communication and/or antivirus preventing intrusion of unwanted binary code into the device and/or it communication. The security may also correct mistakes created during the communication. The security may also block connection of unauthorized/unwanted external device to the device. According to FIG. 4 the security may be located in the communication diagram between the master unit and a communication interface. The security may also be part of a user, a service and/or a sale. According another possible embodiment the security may be located also between the communication interface and a communication medium, the therapy generator and/or may be part of them.

The communication interface may include hardware and/or software. The communication interface enables to provide transfer of communication signal between at least two different parts of the device or between part of the device and the communication media. The communication interface may translate communication signal into readable form for both of communicating sides. The communication interface may be e.g. modem providing communication between the device and online network or server. According some embodiment The communication interface may be part of the master unit, the therapy generator, and/or other parts/features of the device.

The communication medium may be medium transferring communication data. The communication medium may be used in communication between the device and the user, the service and/or the sale. The communication medium may be e.g. wire, any conductive connection, server, some kind of network on principle e.g.: RF waves, acoustic waves, optic waves, GSM, 3G, 4G, HUB switch, Bluetooth, Wi-Fi which may include one or more servers.

Communication data/information may be redirecting to individual parts of the device and/or to individual end users like e.g. the user, the service and/or the sale; by the master unit, the communication medium, the therapy generator and/or individual end user(s). For example Server may filter select data for the user and filter other communication information that will be redirecting to e.g. the service, control unit and/or other parts of the device.

Figure 4:
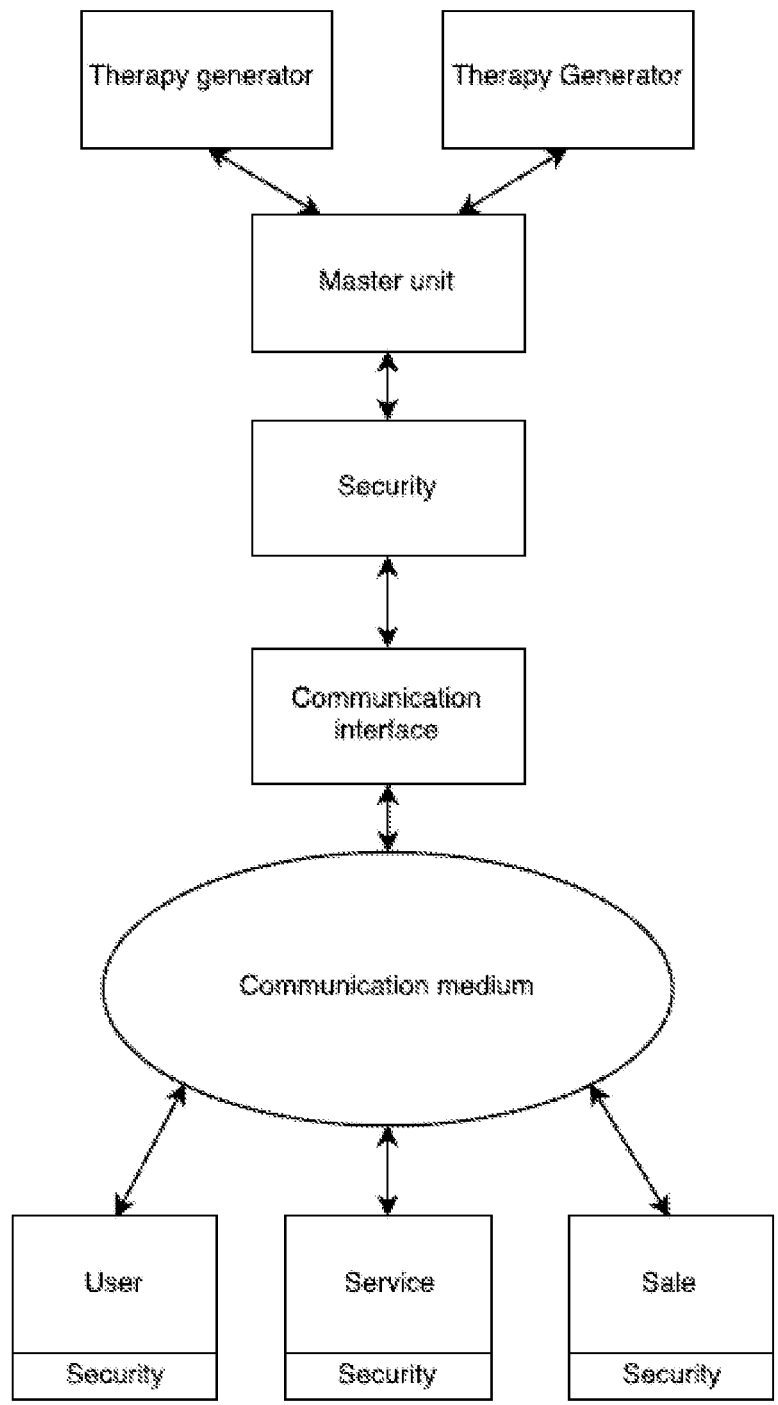
FIG. 4 is schematic illustration of one possible communication between parts of the device and also external devices with remote access.
Figure 5:
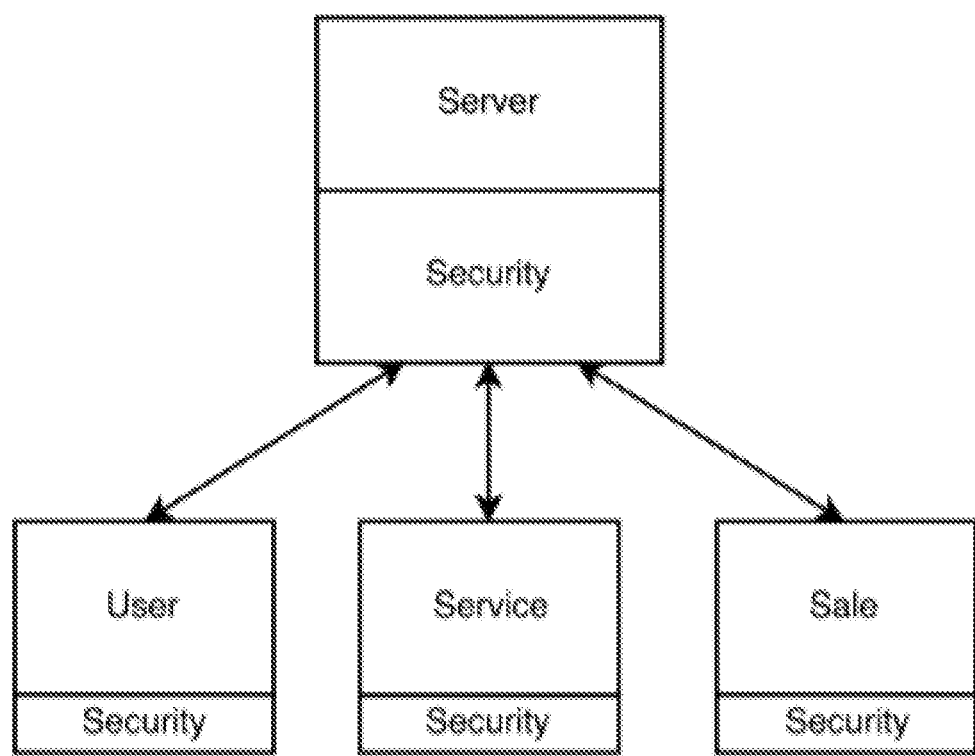
FIG. 5 is schematic illustration of one possible communication diagram between server and part of the device.

According FIGS. 4-5 box the user represents user's communication device (laptop, mobile, tablet, etc.) that may send information to the device and/or receive information from Information provided by this communication channel may be e.g. type of treatment protocol, treatment effect, treatment parameters, feedback information, schedule of treatments, recommendations of behavior before and after the treatment and/or other. Some of users information may be sent to the operator and some to the patient e.g. by an app device for mobile, tablet or laptop.

The app for patient may be downloaded to any external device e.g. smartphone, tablet, computer and/or other. Such app may communicate with the device and according protocol, defined by user and/or provider of the device, patient may display some of treatment protocol information e.g. progress of the treatment, treated body part, remaining time of the treatment, heart rate, temperature of patient's body, provided type(s) of treatment energy, wanted treatment effect, comparison of patient's body parameters against previous treatment (like body fat percentage). The app for the patient(s) may inform about the schedule of treatments, recommendations of behavior before and after the treatment e.g. drinking regime, proposed exercises and its frequency and/or other.

According to FIG. 4 the box service represents service department's communication device (laptop, mobile, tablet, etc.) that has authorized access to information about the device. The service department may be e.g. service department of the device provider company. Information provided by this communication channel may be wear and/or consumption of the device and its components, possible software optimization/actualization of the device, errors in the device, providing apps for connection of other external device and/or other.

According to FIG. 4 the box sale represent sale department's communication device (laptop, mobile, tablet, etc.) with authorized access to information about the device. Exchanged information may be e.g.: number, time and/or type of applied treatment. The sale department may send information about e.g.: renting price of the device billing for treatment (described later as billing system), special offer, possible extending parts of the device, apps for the patients to personal smart phones and/or other.

The device may also include black box storing data of the treatment history, communication between individual parts of the device, data for billing system. The data may be accessible to the sale or to the service via the communication medium (e.g. storage cloud and/or to server). System may manage charges for using the device or respective modules of treatment units and provide is to the provider in order to prepare the invoice for renting.

The data from the black box may be downloaded only by verified authorized person e.g. service technician, accountant. Verification of the authorized person may be e.g.: by specific key, by password, by software code of several bits and/or by specific interconnecting cable.

According another embodiment the billing system may be based on credit subtracting from the user account. User's credit may be predefined by provider of the device e.g. producer of the device; and/or may be recharged during the time of use. Credits may be subtracted according to chosen treatment protocol. Credit value for treatment selected by user may be displayed to user before treatment starts, during the treatment and/or after the treatment. If the credits in the user account run out the device may not enable any further treatment until credit recharge. As it is illustrated on the FIG. 4, communication between individual boxes may be bidirectional. According FIG. 4, secured access of User, Service, and/or Sale may be used to input and/or received information. Such information may be transferred and/or may be also processed through Communication medium (e.g. in the server) and/or communication interface and/or master unit where each information is sorted and decided where should be transferred or stored.

Connection between User, Service, Sale and Communication medium and/or connection between Therapy generator and Master unit may be secured by Security to provide safety communication and eliminate errors. Security may be also implemented between Master unit and Communication interface and/or between Communication medium and Communication interface.

Another possible communication between the user, the service and/or the sale to the device may be provided by server (communication medium) illustrated in the FIG. 5. The server may have implemented the security. The security may or may not be also implemented in individual access of the user, service and/or sale.

Figure 6:
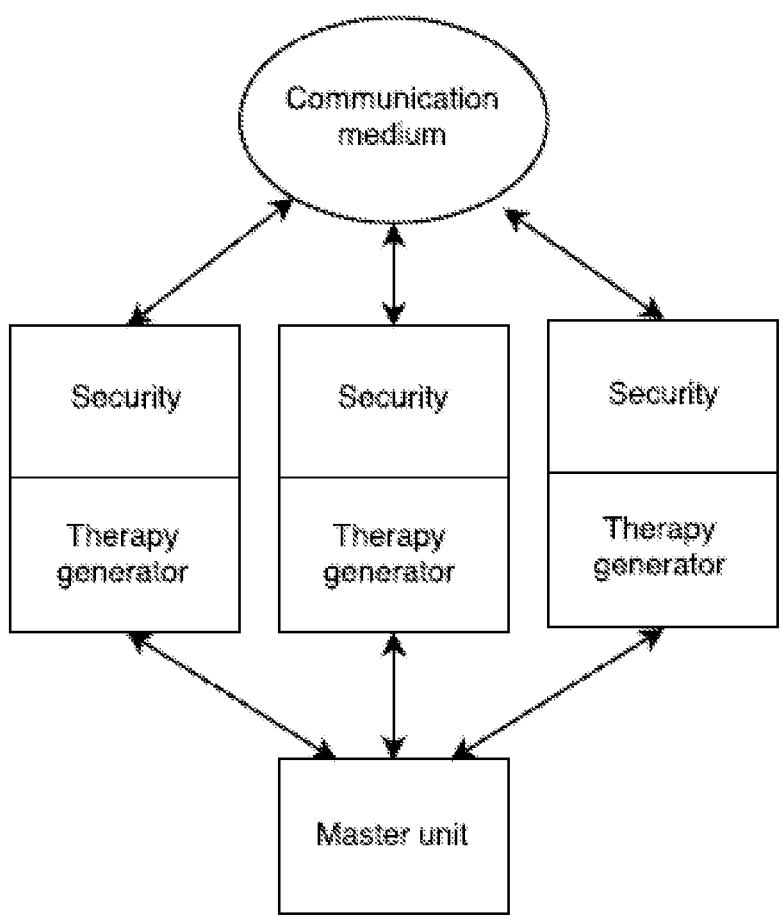
FIG. 6 illustrates communication between communication medium, therapy generator and master unit.
Figure 7:
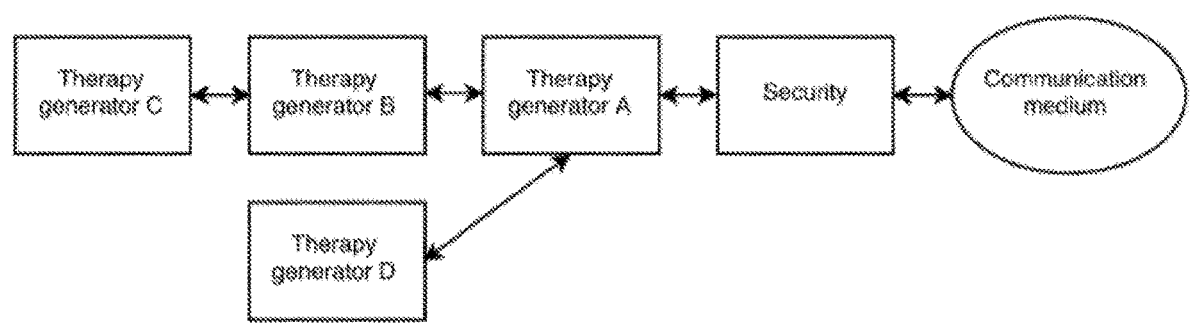
FIG. 7 is schematic diagram of serial communication between communication medium and therapy generator.

According another embodiment depicted in the FIG. 6 the communication medium may communicate with Therapy generator(s) and Therapy generator(s) may communicate with the master unit. According such embodiment communication information from the communication medium may be verified by the security before the treatment generator send communication information to the master unit. FIG. 7 is schematic diagram of serial communication between communication medium and therapy generator. The therapy generator A may communicate with at least one more therapy generator. Subsequent therapy generator B may also communicate with one or more therapy generator(s) e.g. a therapy generator C that does not directly communicate with the therapy generator A.

The device includes one or more applicators for directing the treatment energy into the body and a belt for displacing the applicators into the hardware pattern in proximity of the patient's body. Each applicator may provide one or more different type of treatment energies and/or treatment effects mentioned above and may also include a mechanism for cooling and/or heating of the patient surface and/or any part of the device. For example any applicator may cool itself and/or also part of the supporting matrix. Heating and/or cooling of the patient surface may create thermal gradient across the tissue. Controlled cooling and/or heating may create volume with the highest/lowest temperature on the surface of the patient or may create in the volume with the highest/lowest temperature located under the surface of the patient.

The applicator may include one or more sensors providing feedback information processed by processor and/or external device.

The applicators may have different sizes and shapes. Some of the applicator may have several square millimeters of the active surface. Active surface is the side of the applicator oriented to the patient's surface and it is the part of the applicator which directs the treatment energy into the patient's body. Active surface of the applicator may have more than 10, 40, 50, 100, 200, 300, 500 centimeters square.

Applicators may have different shapes. Some of them may have active surface with symmetrical shape (e.g.: square, circular, elliptical, triangular, teardrop, rectangular, spidery and/or other types) and some of them may have asymmetrical shape of active surface.

Curvature of the active surface of the applicator may be different than curvature of other parts of the applicator. Active surface of the applicator may have regular curvature (e.g.: convex, concave, flat, partially elliptical etc.) and/or irregular curvature (e.g.: partly spherical, pointy, wavy, with some ridge etc.). Curvature of the active surface may also be composition of several different curvatures. Active surface of the applicator may have at some area of active surface different curvature than is curvature at another specific area of the same applicator. Curvature may create specific shape on the active surface of the applicator. Some types of applicator's curvature may improve contact with the patient surface, may modify provided treatment energy delivered to the patient, may increase treatment comfort, may be increase treatment efficiency (e.g. design providing massage of the patient's surface) and/or may improve collecting feedback information (e.g. protruding sensor). Curvature of the active surface may also sets working distance of the applicator and/or may enable air (and/or liquid) flow under the applicator. In some embodiments the applicator curvature across its active surface may be changeable during the time and/or curvature may be used in order to provide massage of the patient.

Massage of the patient's soft tissue may be also provided by e.g.: suction mechanism that creates different air pressure above the patient skin, by mechanical pressure of at least one massage element; massage by switching between parts of the device that creates mechanical pressure, massage by stimulation neuromuscular plaque and/or muscle fibers, massage by acoustic waves and/or ultrasound waves. In order to provide patient's massage and/or other treatment effect design of the applicator's active surface may be adapted to specific treatment energy source.

According preferred treatment pattern massage may be provided in order to stimulate lymph and/or blood flow in direction to lymph node and/or in direction to hearth.

A massage element is a part of the device that creates mechanical pressure on the patient's surface e.g. protrusion on the applicator's active surface that may be movable.

Active surface of the applicator may be designed from material that is able to adapt to any curvature of the body (e.g.: memory foam, elastic active surface of the applicator, and/or any other material).

Active surface of the applicator may be modified. Such modification of applicator's active surface may be provided by interchangeable attachments and/or by exchangeable different types of spacing objects located between patient's body and applicator's active. Modification of applicator's active surface may be provided before, during and/or after treatment. Spacing object may be also part of the supporting matrix.

Active surface of the applicator may also contain one or more apertures of different sizes and shapes. Size and shape of one or more apertures may by variable during the time of the treatment. Apertures may be used to e.g.: provide air and/or liquid flow, may cool/heat patient's surface, supply active substances as it is described in U.S. Provisional Application No. 62/331,060 incorporated here in reference.

Also sizes and shapes of individual treatment energy sources may be variable e.g. RF electrodes as a source of RF treatment energy may have variable surface it is described in U.S. patent application Ser. No. 15/584,747 incorporated here in reference.

Figure 11:
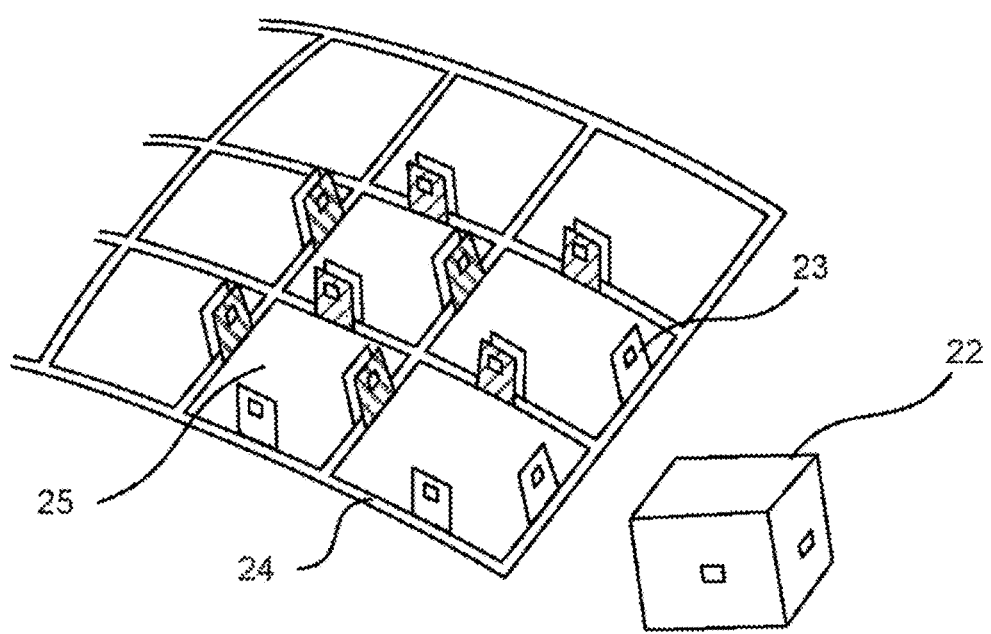
FIG. 11 illustrates one example of supporting matrix and one applicator

In the FIG. 11 is illustrates one example of supporting matrix and one applicator. The applicators 22 may have different sizes and shapes and may be attached by fastening member 23 to supporting matrix 24 across one or multiple applicator's spots 25. As a result, so-called plug and play methods may be used to modify hardware pattern of the applicators attached to patient and/or to supporting matrix (sorting and/or choosing of the applicators). This plug and play method provides a large scale of modularity. The supporting matrix and/or any processor may recognize which applicator is positioned or fixed in which slot in the supporting matrix. Feedback sensor(s) and/or user may also determine which body part is going to be treated.

In an exemplary embodiment the applicator after connection to supporting matrix is identified based and master unit is capable to recognize the parameters including at least one of: kind of treatment energy source/s in applicator, parameters adjustable for treatment, wear of applicator, wear of components in applicator, location of the applicator in the support matrix.

According some embodiment applicator's spot size and/or shape may be adjusted according applicator design before and/or during the treatment. Some type of supporting matrix may enable attached applicator to arbitrary position without limitation of placed applicator's spots. Such supporting matrix may fix applicator(s) to arbitrary applicator's spot by removable fastening member and/or chemical magnetic, electric, and/or suction mechanism, by inserting an applicator into the pocket in the support matrix, by Velcro, loop tape, by magnet, by tacks and/or by any other one or more fastening member. Such supporting matrix may also include multiple holes that enables mechanical fastening of fastening member or applicator with fitting specific protrusion. According some embodiment supporting matrix may not be divided by any applicator's spots.

Some parts of the supporting matrix may be created of flexible, elastic and/or rigid materials e.g.: polymeric materials, ceramics, textile materials, conductive parts and/or other materials. The supporting matrix may be at least partially flexible and/or elastic to provide improved contact with the patient body and/or set appropriate working distance for one or more applicators.

The support matrix may also contain apertures of different sizes and shapes. The support matrix may include system for moving with the applicator to move across the belt area, one or more sensors, processor and/or memory. In some embodiment mechanism of moving with attached applicators and/or treatment energy sources may be provided according defined pattern. Trail for the applicator may be created by some system of rails, by movable one or more component of the supporting matrix (e.g: applicator may be moved along them by mechanical forces based on pressure and/or tensile forces) and/or by trail created from conductive elements and applicators may be moved along them by electric, magnetic and/or electromagnetic forces caused by powering such conductive elements.

Moving of one or more applicators and/or treatment energy sources across the patient body may also be provided by moving of the supporting matrix. Move of the supporting matrix may be provided by expansion and/or shrinking of some parts of the supporting matrix and/or by moving with the supporting matrix along the spacing object (e.g. by mechanic, electric, magnetic and/or combination of these forces) and/or by attaching supporting matrix to an another movable parts of the device (e.g.: mechanical arm, construction on rails etc.)

The supporting matrix may include conductive parts that may provide communication between e.g.: applicators, applicators and control unit, applicator(s) and treatment unit and/or applicator(s) and external device. Conductive parts in the supporting matrix may also provide power supply to the applicator(s). Applicator(s) may include rechargeable one or more batteries as a source of energy. These batteries may be recharged trough the supporting matrix and/or through the spacing object.

According another embodiment supporting matrix may also determine applicator(s) e.g.: location in the supporting matrix, type of the applicator, contact with the supporting matrix, and distance from the patient's surface; supporting matrix may also provide feedback information and/or other features.

This sheet may contain conductive components. A hardware pattern may be created by placing of the applicators into the belt (e.g. supporting matrix) attached to patient's body. According to one embodiment the master or control unit may propose ideal hardware and/or treatment pattern based on selected treatment protocol in order to optimize selected treatment effect(s) of selected body part(s). The master or control unit may take into account also supportive information parameters of the patient like age, sex, weigh, height, BMI, skin type and others.

The master unit and/or control unit may also propose one or more treatment effects, treatment protocol and/or treatment pattern according hardware pattern of the belt. According specific embodiment may be needed to select treated body part and/or the device may be able to determine body part according feedback information from at least one sensor.

A treatment pattern may be created by several possible ways. Treatment pattern may be created by moving with at least one treatment energy source(s) and/or applicators across the patient's surface. Moving with the treatment energy source(s) may be provided within the applicator and/or by moving with one or more applicators. Moving with the applicators may be provided e.g. within the supporting matrix that may include movable parts. Moving with the applicator(s) and/or treatment energy sources across the patient's surface may be provided e.g.: by movable component of the applicator and/or supporting matrix pushed by air/liquid pressure, by electromotor, by electric and/or magnetic forces causing move of movable part of an applicator, supporting matrix, and/or move of an applicator. Moving of the treatment energy source and/or the applicator may be based on principal described in U.S. patent application Ser. No. 15/433,210 incorporated here in reference.

According to the proffered embodiment the treatment pattern may be created by switching on/off or varying intensity of delivered treatment energy between individual and/or groups of treatment energy sources. Switching between treatment energy sources or varying intensity of delivered treatment energy between treatment energy sources may simulate movement of at least one treatment energy source guided by operator. Creating of treatment pattern may be based on principal described in U.S. patent application Ser. No. 15/433,210 incorporated here in reference.

Treatment pattern created by at least one but more preferably at least two types of treatment energies by at least two treatment energy sources is characterized by at least one, more preferably at least two target spots of specific and/or different treatment energy sources that may vary treatment energy intensities with regard to time and/or spatial coordinates—usually location in patient's tissue. The target spot is a location where treatment energy is delivered and which has absolute value of provided treatment energy intensity above zero. The target spot may be created by providing focused and/or non-focused treatment energy. A center of target spot is spatial coordinate where absolute value of provided treatment energy intensity is the highest (e.g. center of the treatment energy source). In one embodiment the treatment pattern may be created by a continuous or discontinuous trajectory of the target spot(s) across space coordinates. The target spot(s) may vary intensity of delivered treatment energy during the trajectory described by treatment pattern. Move of the target spot may be provided by moving of at least one treatment energy source that usually creates the continuous trajectory of target spot(s) and/or by varying treatment energy intensities between at least two treatment energy sources wherein the target spots may overlap and create continuous trajectory and/or may not overlap that creates the discontinuous trajectory of target spot described by treatment pattern. Changing spatial coordinates of the center(s) of target spot(s) across patient's tissue during the time may be described by treatment pattern speed. Treatment pattern speed may be also described as ration of target spots distance and time delay. Spots distance is distance between the centers of target spots of at least two nearest treatment energy sources reaching maximum treatment energy intensity during shortest time delay. Time delay may be described as time delay between above mentioned centers of target spots reaching their absolute values maximums of treatment energy intensities. Average treatment pattern speed may be in the range between 0.1 cm·s−1 and 50 cm·s−1 or more preferably in range between 1 cm·s−1 to 30 cm·s−1 or the most preferably in range between 2 cm·s−1 to 15 cm·s−1.

Treatment pattern speed may be constant and/or may vary during one treatment pattern.

Treatment pattern provided by first type of treatment energy may be also accompanied by other types one or more treatment energies provided to the patient's tissue. Such other treatment energies may follow treatment pattern of the first treatment energy with the same or different treatment pattern speed and/or may follow different treatment pattern(s).

Treatment patterns may also be created by varying treatment energy intensities of multiple treatment energy sources that reaches their maximums of absolute value of treatment energy intensities at the same time. According such example treatment pattern speed may be described as was described above as ration of target spots distance and time delay.

Treatment pattern may change during one treatment based on one or more treatment protocols.

During one treatment may be provided one or more treatment patterns simultaneously and treatment pattern may also overlaps and/or build on yourself.

Figure 8:
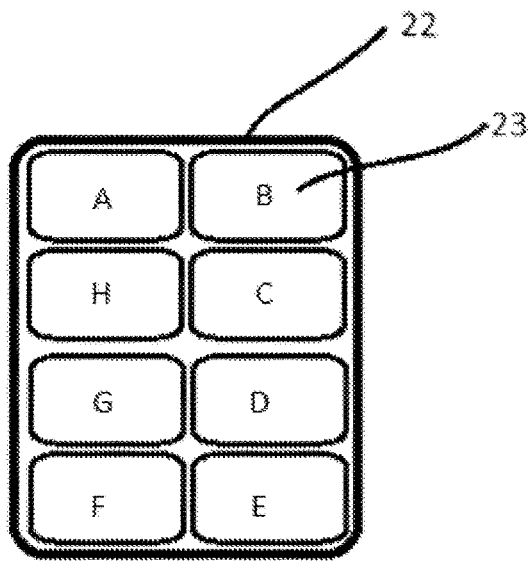
FIG. 8 illustrates active surface of an applicator with multiple treatment energy sources.

Applicator including more than one treatment energy source may create its own small treatment pattern by switching between individual treatment energy sources. Small treatment pattern created by one applicator may be part of bigger treatment pattern created by switching between individual applicators. In FIG. 8 where 22 symbolize applicator's active surface with multiple treatment energy sources A-H and 23 symbolize one of the treatment energy sources. Applicator may contain treatment energy sources with different shapes. Number of treatment energy sources in one applicator is not limited. Switching on/off between treatment energy sources, changing of the treatment energy intensity between treatment energy sources and/or moving with the treatment energy sources during the treatment may be defined by treatment protocol. The treatment energy sources of at least one applicator that can work simultaneously, with some overlay and/or sequentially during the treatment. Also one or more treatment parameters of the procedure may be adjusted before and/or during the treatment.

The applicator and/or treatment energy source may provide multiple treatment effects. According one embodiment one applicator may include treatment energy sources producing one or more types of treatment energies e.g. one treatment energy source may produce shock waves, ultrasound and/or acoustic waves during one treatment.

Time intervals between the power amplitudes of delivering treatment energy to the patient's body by individual treatment energy sources may overlay and/or may be divided by pause time interval in the range between 01 ms to 15 s or 1 ms to 5 s or 100 ms to 3 s.

Figure 15:
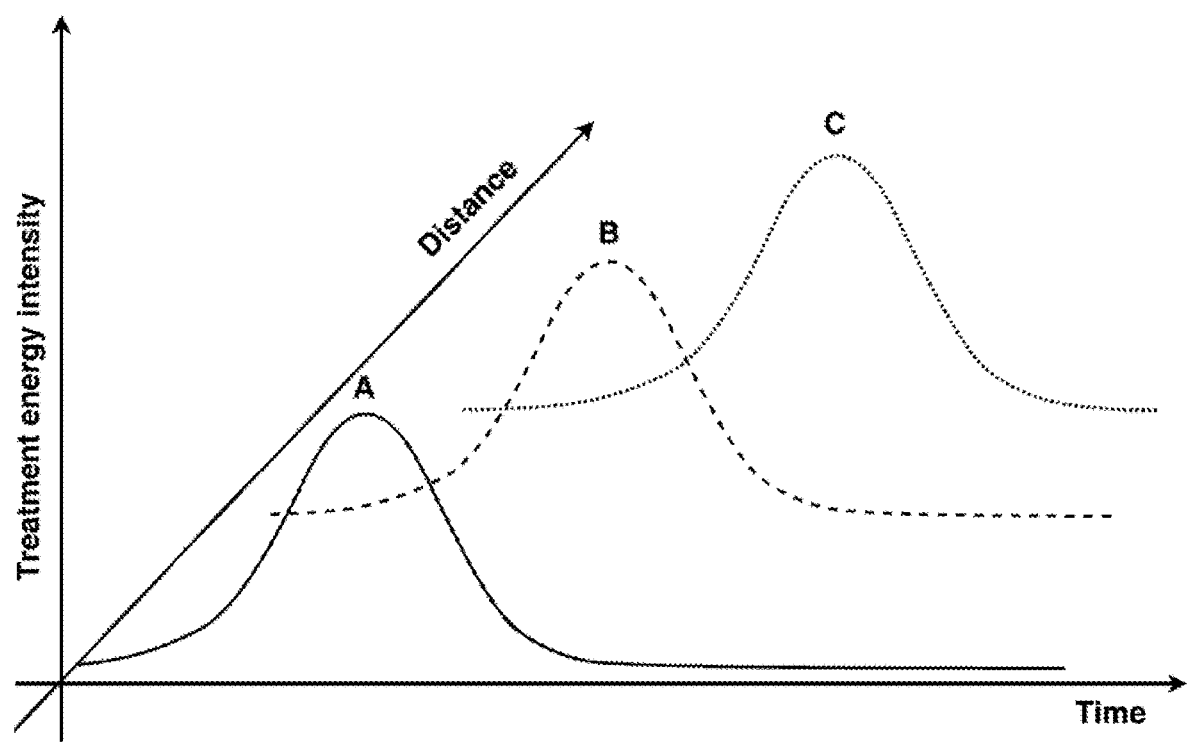
FIG. 15 illustrates possible example of three functions of treatment energy intensities depending on time provided by individual treatment energy sources arranged in hardware pattern.

FIG. 8 describes one possible displacement of treatment energy sources. The respective treatment energy sources may provide a treatment pattern by varying intensity of delivered treatment energy between the respective treatment energy sources as depicted in FIG. 15. Treatment energy source A may temporarily increase intensity of provided treatment energy A to patient's body, see peak A. After treatment energy intensity A rises above the initial treatment energy intensity value, treatment energy intensity B provided by treatment energy source B, see peak B, may also starts to temporarily rise. The same principal as was described for treatment energy source A and B may be repeated for treatment energy sources C see peak C, D, E, F, G, H and that may create circular treatment pattern with clockwise direction that may be repeatedly used. The treatment patter speed between treatment energy sources A and B according FIG. 15 may be count as distance between maximums of peaks A and B in ration with time delay between peak A and peak B reaches their maximums.

The various other treatment patterns as described in this document may be used.

According to another embodiment peaks A, B and/or C in the FIG. 5 may represents different types of treatment energies e.g.: RF, ultrasound and/or shock wave. Peaks A, B and/or C may have the same and/or different profiles, maximal values and/or integral values. Treatment energy intensity peak may have no overlap and/or may have at least partially overlap from a spatial coordinates and/or time point of view.

According treatment pattern in FIG. 15 peak of the first treatment energy intensity (peak A) may starts to decline sooner, at the same time or after the second treatment energy intensity (peak B) starts to decline and/or reaches its maximum intensity value.

Also target spots created by the same and/or different treatment energy types during treatment pattern may have no overlap and/or may at least partially overlaps in the patient's tissue.

According to one preferred embodiment the pattern with at least two different energy sources providing different treatment energy may be used.

Figure 9:
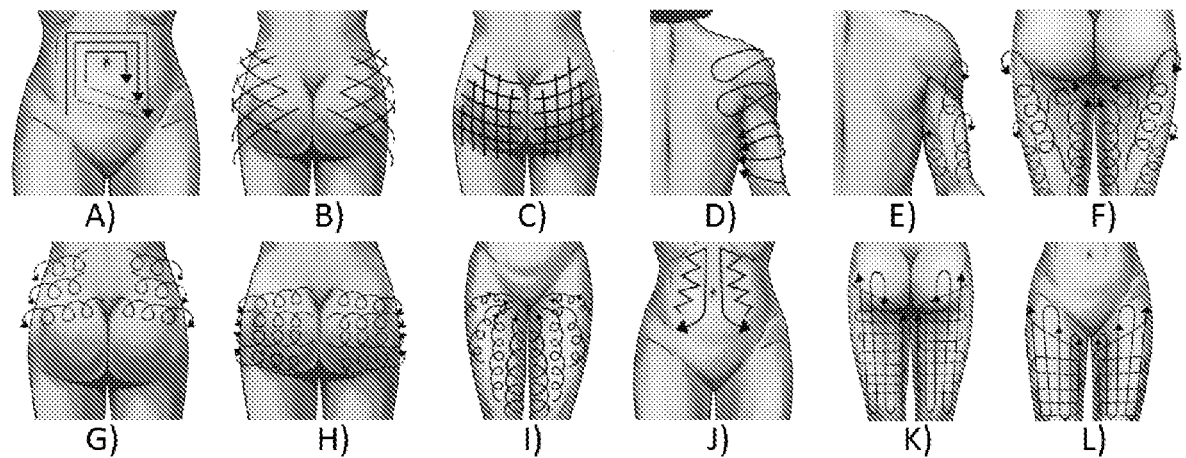
FIG. 9 demonstrate several treatment patterns provided across the patient's surface FIGS. 10 A and B illustrates treatment patterns provided into depth of the patient's tissue.

The pattern with at least two different energy sources providing different treatment energies may provide synergic effect in influencing the treatment results. One illustrative example of such synergy may be a pattern consisting of RF and focused ultrasound energy sources where the ultrasound energy source provide heating in the target spot and then the RF is more absorbed by the preheated tissues, while continual simulation the movement according to the chosen pattern Possible treatment patterns see FIG. 9 may simulate linear moves of treatment energy source(s) across the patient's surface-See FIG. 9A-C, FIG. 9D simulates curvilinear moves, FIG. 9 E-I simulates several types of circular moves, and/or FIG. 9J-K simulates combination of linear and curvilinear moves.

Treatment pattern may not be limited only by moving with the treatment energy target spot according two dimensional moves with regard to patient's surface. Treatment pattern may determine depth of treatment energy target spot. One illustrative example may be a pattern consisting of RF and focused ultrasound energy sources where the focused ultrasound energy source provide heating in the target spot at one depth and then the RF is more absorbed by the preheated tissues, while continual simulation the movement according to the chosen pattern, which simulates movement of target spot in tissue in one, more preferably two, most preferably three dimensions. The depth and planar location of target spot may vary in time based on selected treatment protocol.

Figure 10:
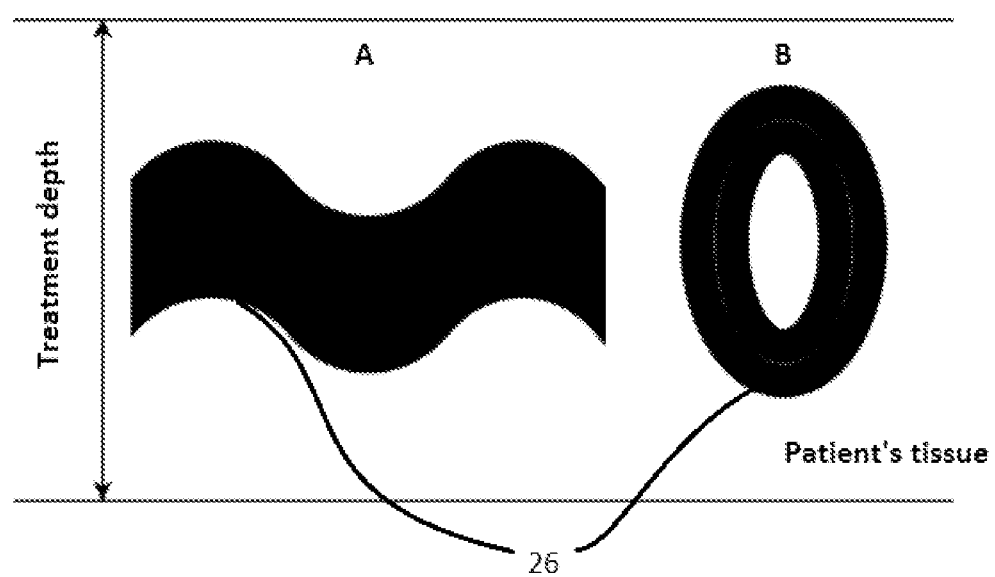

Treatment pattern with and/or without defined treatment depth pattern may be cyclically repeated. FIG. 10A illustrate one possible example of short sequence of treatment pattern with varied treatment energy focus depth 26 according changed horizontal coordination of treatment energy target spot in the patient's tissue. Horizontal coordinates are parallel to patient's surface curvature under the belt at every space coordinate under the belt. For example horizontal coordinates in patient's hips area according some patient's body type may be described as convex surface area in Cartesian coordinates. FIG. 10B illustrate one possible example of treatment pattern with varied treatment energy focus depth 26 during the time and changed horizontal coordination in the patient's tissue. Treatment energy focus depth 26 may be also varied during the time of the treatment without regard to changed horizontal coordinates of the treatment energy target spot. Depth of treatment energy target spot may be varied also for non-focused treatment energy e.g. by changing intensity of delivered treatment energy, changing wavelength, polarization of treatment energy, distance between electrodes providing RF treatment energy and/or by changing other parameters of delivered treatment energy to the patient's body.

Depth of treatment energy target spot may be varied also by changing parameters of patient's tissue for example by providing another treatment energy e.g. heating or cooling of the patient's tissue that may increase penetration of the RF waves, by apply electric field that may influence dielectric behavior of the patient's tissue.

various kinds of treatment patterns may be provided by various kinds of hardware patterns. Cooperation of hardware pattern and treatment pattern may significantly improve treatment result(s), shorten treatment time and/or may increase treatment safety. Exemplary variants of hardware patterns providing a treatment patterns are provided below. According one exemplary variant may be sequential and/or simultaneous applying of one or more treatment energies heating the patient's tissue and/or damage tissue cells with treatment energy that accelerates metabolism, blood flow, lymph flow and/or accelerate removing of damaged cells. Simulated move trajectory may be like is illustrated in the FIG. 9A-L. Example of such treatment pattern may be alternately placed treatment energy sources providing e.g.: RF, shock waves, ultrasound, light; and treatment energy sources providing massage and/or muscle stimulation like e.g. suction mechanism, muscle stimulation magnetic field, muscle stimulation electrode, movable massage element providing mechanical pressure and/or other.

According one exemplary variant may be used one or more treatment energies that heats patient's tissue and/or damage tissue cells in combination with at least one treatment energy that accelerate metabolism, blood flow, lymph flow and/or accelerate removing of damaged cells. Combination of such at least two different treatment energies may be simultaneous, with some overlay, sequentially and/or may be apply in close proximity that allows the synergic effect of at least two different types of treatment energies. Applicators and/or treatment energy sources in applicator may be distributed in 2D and/or 3D matrix. For example applicators including different types of treatment energy sources may be placed in close proximity to supporting matrix and/or to patient's body and coordinated variation of treatment energy intensities may simulate move of at least one applicator as it is illustrated in the FIG. 9A-L.

Example of such treatment pattern may be alternately placed treatment energy sources providing e.g.: RF, ultrasound, shock wave or light in combination with treatment energy sources providing e.g.: acoustic wave, massage and/or muscle stimulation by suction mechanism, magnetic field, current, movable massage element providing mechanical pressure and/or other.

Figure 13:
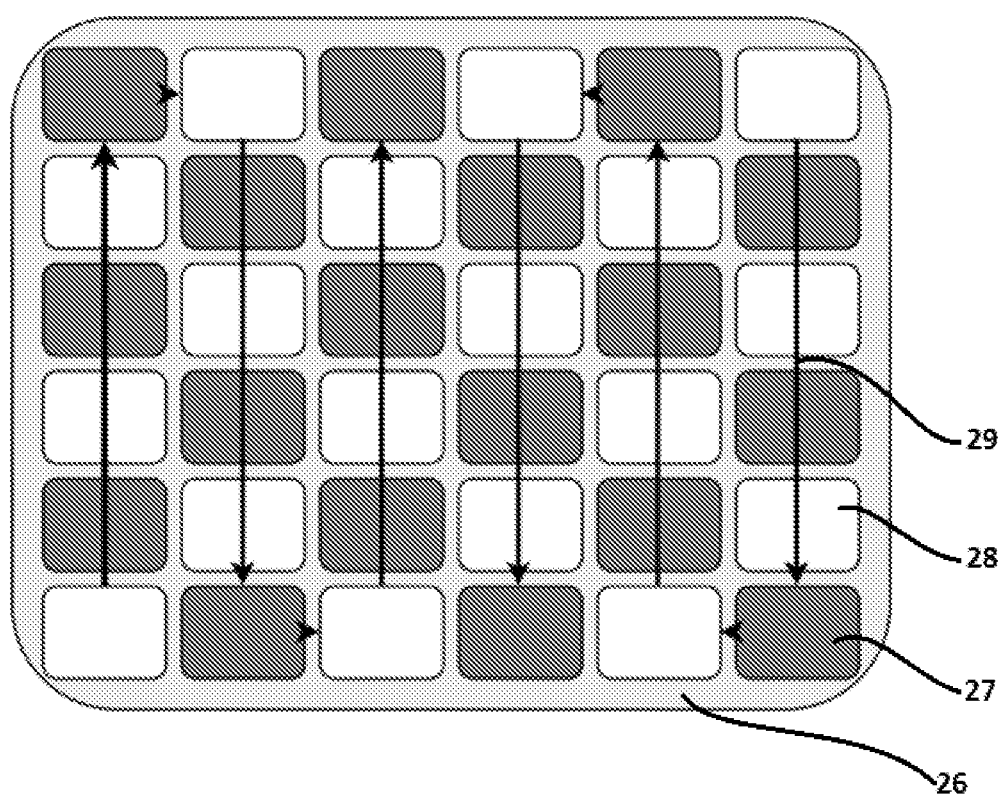
FIG. 13 illustrates one of possible symmetric hardware and treatment pattern.
Figure 14:
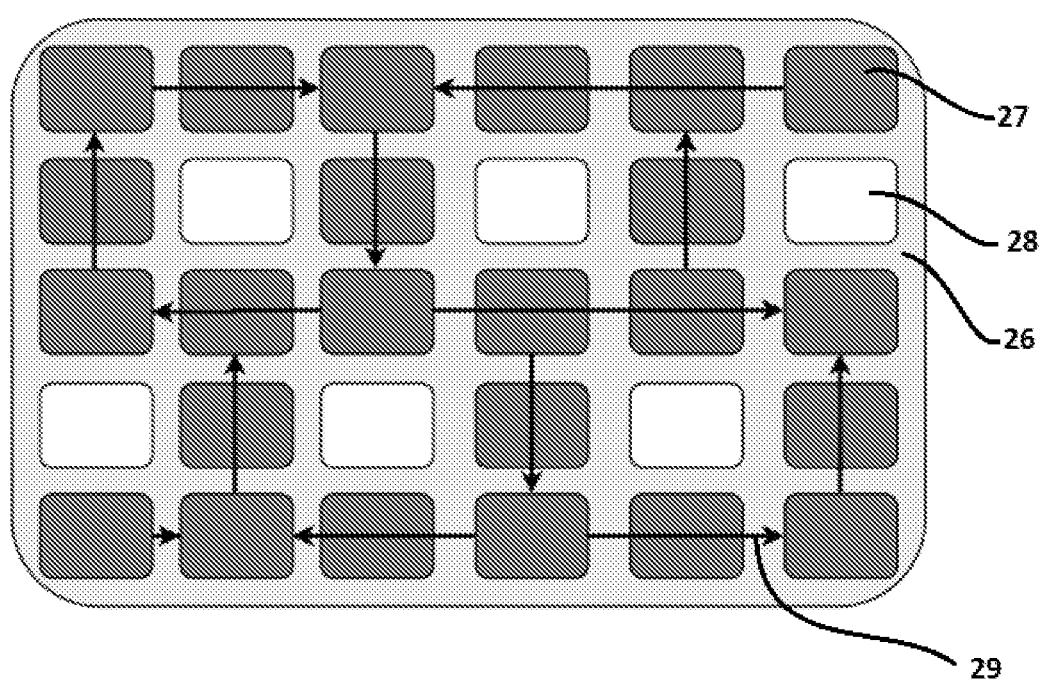
FIG. 14 illustrates one of possible symmetric hardware pattern and asymmetric treatment pattern.

Placement of different treatment energy sources/applicators may be one of the most important parameter of the treatment. FIGS. 13 and 14 illustrate two types of treatment patterns. FIG. 13 illustrates alternately placed treatment energy sources 27 providing heating of the patient's tissue, creating cell damage and/or tissue structure damage e.g. by: RF, ultrasound, shock wave or light etc. in combination with treatment energy sources 28 providing acoustic wave, massage, stimulation of lymph flow, blood flow and/or metabolism stimulation. Treatment energy sources 27 and 28 may be attached to supporting matrix 26. Arrows 29 symbolize direction of treatment pattern and orientation of treatment pattern speed therapy.

In FIG. 13 is provided symmetric treatment pattern simulating linear moves of two treatment energy sources. According other example treatment energy sources 27 may be placed around the treatment energy sources 28 see FIG. 14. Symmetric placement of treatment energy sources and/or applicators may create also asymmetric and/or partially symmetric treatment pattern depends on resulting pattern created by varying intensities between multiple treatment energy sources during the time, see arrows 29. Resulting pattern according arrows 29 in the FIG. 14 imitate partial symmetric circular moves by multiple treatment energy sources.

According to FIG. 14 treatment energy intensities provided by treatment energy sources 27 may simulate circular moves and treatment energy sources 28 may provide continual and/or pulsed blood, lymph and/or metabolism stimulation.

According to another embodiment treatment pattern(s) may be also created also by treatment energy source that change location of treatment energy target spot in the patient's tissue by its movement. Changed may be target spot volume, target spot depth, target spot shape and/or target spot coordinates according horizontal plane in the patient's tissue.

Treatment patterns described by FIGS. 13 and 14 are not limited examples.

According to one exemplary variant one or more treatment energies may provide treatment of hypodermal tissue and one or more different treatment energies may provide treatment of epidermal or dermal tissue. Combination of such at least two different treatment energies may be simultaneous, with some overlay, sequentially ensuring faster treatment of more than one tissue problems. Example of such treatment pattern may include displacement of treatment energy source providing hypodermal treatment by RF, UZV, shock wave, light or magnet and treatment energy source providing epidermal or dermal treatment by light, plasma, RF.

According to another exemplary variant one or more treatment energies may provide treatment of epidermal tissue and one or more different treatment energies may provide treatment of dermal tissue. Combination of such at least two different treatment energies may be simultaneous, with some overlay, sequentially ensuring faster treatment of more than one tissue problems. Example of such treatment pattern may include displacement of treatment energy source providing epidermal treatment by light or plasma; and treatment energy source providing epidermal or dermal treatment by RF, UZV, shock wave, light.

Described variants may also damage cells and/or tissue structure by the first treatment energy source and accelerate healing of the tissue by the second treatment energy source.

Attaching of the applicator to the belt or belt to the patient may be provided by: gravitational force, by high roughness of a contact surfaces, by electric forces, by magnetic forces, by chemical bounds (e.g. interaction between polar molecular groups on at least one contact surfaces) via fastening member(s) e.g. working on clam mechanism and/or its combination. Fastening member may be permanent or removable part of any applicator, supporting matrix, spacing object and/or any other part of the device (e.g. treatment unit(s) and/or mother case). Fastening member may be adhesive polymer or copolymer (e.g. poly(styrene-ethylene-butylene-styrene) and/or others) which is located at the one or more contact sides of fastening member. Fastening member may also be design as: as rails, sticky layer between two contact sides, elastic, partially elastic and/or non-elastic stripes, Lace, Velcro, zipper, snap, clamp, tacks, as member creating lower air pressure between contact surfaces e.g.: by suction mechanism; by layer providing interaction between polar and/or non-polar group on the contact surfaces and or member using physical (e.g.: electric, magnetic forces), chemical, mechanical interaction between fastening member(s), parts of the device and/or between patient surface.

Fastening member may have different sizes, shapes and in one embodiment may be combined different types of fastening members.

The applicator(s) may be attached at the right working distance by fastening member designed as one or more stripes located in front and/or back side of the applicator. Suitable elastic materials are elastomers or also elastic fabrics. The elastic belt material also adapts to respiratory movements and/or other movement of the patient. Fastening member designed as stripes may also include conductive component(s) that may be connected and/or communicate with supporting matrix and/or other part(s) of the device. Such conductive components may also recharge e.g. applicator(s) and/or supporting matrix.

Supporting matrix may hold one or more applicators in touch with patient's body surface and/or it may also hold one or more applicators at an optimal working distance from the patient surface. The patient's surface is typically the epidermis of the patient. However, the patient's body surface may alternatively be some spacing object e.g.: clothing worn over the skin, a sheet, pad or other thin (0.1-2 mm) covering over the skin, and/or a thicker spacing object. The spacing object may provide suitable working distance for the applicators, may provide heating/cooling of the patient body, massage of patient's soft tissue, may provide several modifications of delivered signal to the patient soft tissue e.g.: polarization, filtration of provided signal to the soft tissue, better transfer of the signal to the soft tissue, changing direction of pointing vector of provided electromagnetic field, prevent of edge effect and/or others as described in U.S. Provisional Application No. 62/331,072, incorporated herein by reference. Spacing object may be located between any parts of the device e.g. between supporting matrix and applicator(s) and/or between patient and parts of the device e.g. between patient and supporting matrix and/or between patient and applicator(s). Because of mechanical, structural, physical and/or chemical properties of this spacing object, spacing object may provide and/or improve attachment of any parts of the device and/or parts of the device and patient body surface together.

The belt may at least partly encircle any part of the patient's torso and/or limb.

Feedback information may be collected by different types of sensors and may have different characters e.g.: biological, chemical, physical etc. One or more sensors may be located in supporting matrix, in one or more applicators and/or may be located externally out of the belt (e.g.: optical, sound and/or others located around a patient. One or more sensors may control treatment parameters e.g.: intensity of delivered energy into the tissue, sequence of applied treatment energy, changing parameters of the delivered signal and/or switching on/off of different treatment energy sources and/or others. The device may contain different types of sensors for monitoring device parameters, monitoring of body biological, physical, chemical and/or other parameters (e.g.: an electrochemical sensor; a biosensor; a biochemical sensor; a temperature sensor; sensor for measuring distance of applicator from the patient surface, from some area of the patient soft tissue and/or from other applicator (determine position of the device with regard to patient's body part); a sensor for recognition of applicator orientation in 3D; rotational orientation sensor; a sorption sensor; a pH sensor; a voltage sensor; a detector of moving velocity and/or change of treatment energy source position; change of focus target area of the treatment energy; photo sensor; sensor measuring fluid viscosity; a camera; a sensor for measuring fluorescence of the patient surface; a sound detector; a current sensor; sensor for measuring of specific heat capacity of human/animal tissue; a sensor for measuring value of magnetic field; sensor for measuring impedance; permittivity; conductivity; susceptibility and/or any suitable sensor or sensors measuring biological parameters and/or combination thereof e.g.: sensor for measuring dermal tensile forces; sensor for measuring the activity of the muscle; a sensor for measuring muscle contraction forces; sensor for measuring pulse of the patient; a sensor measuring skin elasticity. The device may also include at least one contact sensor for monitoring applicator contact with body surface of the patient. Supporting matrix may also recognize type and/or location of the different one or more applicators attached to the supporting matrix.

The applicator(s) may be able to communicate with each other and/or other parts of the device e.g. external device, control unit, treatment unit and/or other as was mentioned above. This communication may provide information from feedback sensors, about position of one or more applicators, 3D orientation of the applicator(s), information about contact of the applicator(s) with the patient and/or supporting matrix, distance from the patient surface, parameters of the treatment protocol, parameters of each applicator and/or other information from one or more sensors. Data from different applicators and/or types of sensors may provide complex information about the treatment and/or treated soft tissue. Information from the sensors may be used to determine which part of the patient is treated, determine the exact composition of treated tissue and/or changes in patient's tissue during the time of the treatment. These sensors may cooperate with one or more treatment energy sources providing and may be used as imaging device of surface and/or deeper layers of the patient soft tissue. Imaging system of the soft tissue before and/or during the treatment may improve safety of the treatment, determine when the treatment is complete, monitor treatment process and/or progress of the treatment. This processed data may be used for adjusting parameters of the treatment procedure, may activate other treatment energy source(s) and/or one or more treatment protocols (activate massage, cooling, heating and/or others) and/or change any other parameter of the treatment protocol. This data may also warn operator and may be used as prevention of health risk and/or may prevent damage any part of the device.

Treatment protocol may include several instructions that define treatment of one or more treatment energy sources and/or applicator(s). Treatment protocol may include information about e.g.: treatment pattern, treatment pattern speed, which treatment energy source(s) are switched on/off and/or parameter of individual treatment energies produces by individual treatment energy source(s). Treatment protocol may also include information about applicator(s) and/or treatment energy source hardware pattern. Treatment protocol may also include information about system of collecting feedback information e.g. which sensor communicate with which part of the device. According some embodiment treatment protocol may also include information how will parts of the device communicate with each other, how will be information during the treatment processed, by which parts of the device and/or treatment protocol may also define priority of commands during the device communication. Another examples of information that may be included in treatment protocol: applied treatment effect(s), shapes and types of a delivered signal of treatment energy into the tissue (symmetrical; asymmetrical; polarized; non-polarized; continual or sequences of signal pulses; timing of the delivered signal; shape of the signal: sine, square, triangle, saw tooth and/or others), define pulse sequences intensity of delivered energy, polarization of delivered electro-magnetic signal, remaining time of treatment procedure, threshold parameters, time and/or sequence of heating/cooling of the soft tissue and/or other parameter that influence treating of the soft tissue by one applicator (e.g.: geometry and position if it is possible to change this parameters and/or other parameters).

Figure 12:
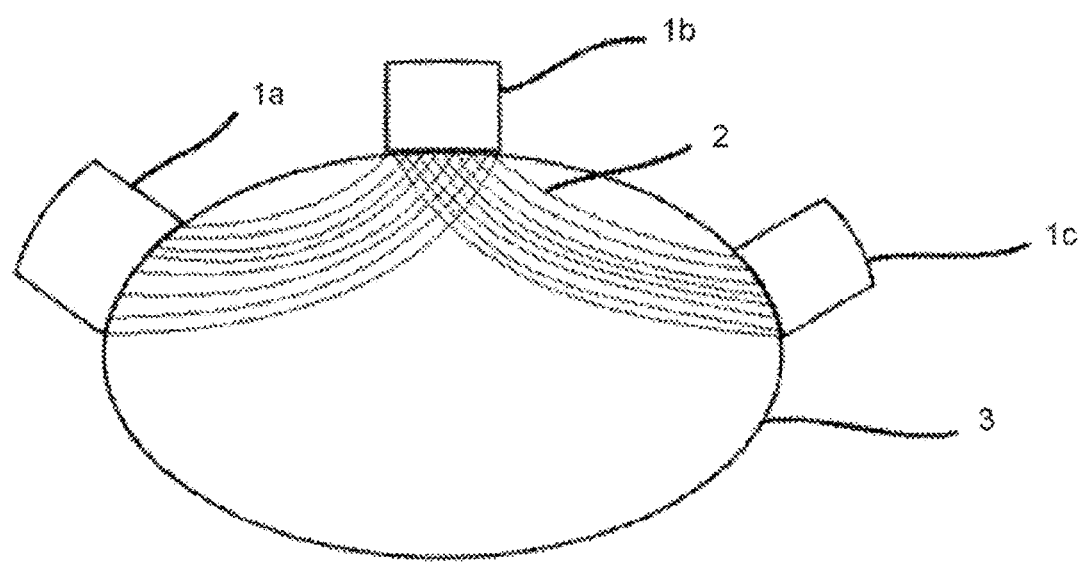
FIG. 12 illustrates multipolar treatment of three cooperating applicators.

Several applicators may cooperate with each other. FIG. 12 describes cooperation of multiple applicators 1a, 1b, 1c that may provide some of treatment energy or energies (e.g. multipolar RF therapy symbolized by field lines 2) to the patient 3. Cooperation of treatment energy sources providing different treatment energies (e.g.: RF, ultrasound, light, acoustic wave, shock wave, plasma, mechanical massage, cooling/heating, electric wield, electric current, magnetic field and/or other treatment energy sources) may be used for better targeting of delivered therapy, better focusing of delivered signal, creating of some gradient in the soft tissue (e.g. thermal gradient, etc.), better homogeneity of provided therapy across large patient area and/or volume of the soft tissue.

According to one embodiment, the cooperation of multiple applicators and/or treatment energy sources may enlarge treatment variability (e.g. treatment depth, focusing, preventing hot spots, may enable provide lower intensity of treatment energy without lowering treatment result), since the electrode of each applicator and/or treatment energy source may represents one pole of multipolar treatment.

Cooperation between applicators and/or treatment energy sources may include transferring of treatment energy, communication information and/or one may provide power supply of another one or more applicators.

Presented description of the device is not intended to limit the invention to these embodiments, but rather to enable any person skilled in the art to make and use this invention.

The invention claimed is:

1. A modular treatment device for improvement of a visual appearance of a patient, comprising:
   a mother case comprising a control unit and a plurality of slots;
   a plurality of treatment units removably connected to the mother case in the slots; and
   an applicator removably connected to the mother case;
   wherein the control unit is configured to detect and configure the plurality of treatment units in the mother case;
   wherein the control unit includes a processor and a memory;
   wherein the control unit is configured to control the plurality of treatment units;
   wherein each of the plurality of treatment units is configured to generate a different type of a treatment energy;
   wherein the applicator is configured to direct the different types of treatment energies to a body part of the patient;
   wherein the control unit is configured to provide one or more predefined treatment protocols to a user via a user interface based on a detection of the plurality of treatment units; and
   wherein the modular treatment device is configured to perform a selected treatment protocol from the one or more predefined treatment protocols in order to improve the visual appearance of the patient.

2. The device of claim 1, wherein the applicator further comprises one or more treatment energy sources providing the different types of treatment energies causing at least one treatment effect in the body part of the patient.

3. The device of claim 1, wherein each of the treatment energies is one of: a radio-frequency, a plasma, an ultrasound, acoustic waves, shock waves, a light, an electric current, a magnetic field, a positive or negative pressure, a heating or a cooling.

4. The device of claim 1, wherein the modular treatment device is configured to provide the different types of treatment energies to the body part of the patient simultaneously during the treatment.

5. The device of claim 1, wherein the modular treatment device is configured to apply the different types of treatment energies to the body part of the patient at the same time, sequentially or with overlay according to the selected treatment protocol.

6. The device of claim 1, further including a belt;
   wherein the applicator is coupled to the body part of the patient with the belt;
   wherein the belt is flexible or partly elastic; and
   wherein the device is configured to be self-operated without needing intervention by professional medical staff after the treatment begins.

7. The device of claim 1, wherein each slot of the plurality of slots comprises a connecting mechanism which is configured to accept any treatment unit from the plurality of treatment units.

8. The device of claim 1, wherein the plurality of slots and the plurality of treatment units comprise at least one of an electromagnetic shielding, a vibration shielding, a thermal shielding or an electrical insulation.

9. The device of claim 1, further including a billing system based on credit subtraction from the user;
   wherein the modular treatment device is configured to transmit information about the selected treatment protocol to the billing system and to subtract credits in the billing system according to the selected treatment protocol.

10. The device of claim 1, wherein the applicator is attached to the body part of the patient with a fastening member.

11. The device of claim 10, wherein the fastening member is a part of the applicator; and
    wherein the fastening member is an adhesive polymer or copolymer.

12. A modular treatment device for improvement of a visual appearance of a patient, comprising:
    a mother case comprising a control unit and a plurality of slots;
    the control unit comprising a processor and a memory;
    first and second treatment units removably connected to the mother case in the plurality of slots;

a first and a second applicator; and
a first and a second treatment energy source;
wherein the control unit is configured to detect, recognize, and configure the first and the second treatment units in the mother case;
wherein the control unit is configured to control the first and the second treatment units;
wherein the first and the second treatment units are configured to generate different types of treatment energy;
wherein the first applicator is configured to be connected to the first treatment unit and the second applicator is configured to be connected to the second treatment unit;
wherein the first applicator includes the first treatment energy source;
wherein the first treatment energy source is configured to provide a first treatment energy to a body part of the patient;
wherein the second applicator includes the second treatment energy source;
wherein the second treatment energy source is configured to provide a second treatment energy to the body part of the patient;
wherein the modular treatment device is configured to provide one or more predefined treatment protocols to a user via a user interface based on a detection of the first and the second treatment units; and
wherein the modular treatment device is configured to perform a selected treatment protocol from the one or more predefined treatment protocols in order to improve the visual appearance of the patient.

13. The device of claim 12, wherein each of the first and the second treatment units comprises a socket or a pin connector configured to be connected to a slot of the plurality of slots of the mother case.

14. The device of claim 12, wherein each slot of the plurality of slots comprises a connecting mechanism which is configured to accept each of the first treatment unit and the second treatment unit.

15. The device of claim 12, further including a communication medium configured to transfer communication data between the modular treatment device and the user or the patient;
wherein the communication medium is a wire, any conductive connection, server, storage cloud, network, RF waves, acoustic waves, optic waves, GSM, 3G, 4G, HUB switch, Bluetooth or Wi-Fi.

16. The device of claim 15, wherein an element of data provided in the communication data between the device and the user is one of: a type of the treatment protocol, the treatment effect, treatment parameters, a feedback information, a schedule of treatments or recommendations of behavior before or after the treatment.

17. The device of claim 15, further including a downloadable app for the patient stored on a non-transitory computer readable medium of an external device;
wherein the app communicates with the device via the communication medium; and
wherein the app comprises a user interface configured to display treatment protocol information selected from: progress of the treatment, the treated body part, a remaining time of the treatment, a heart rate, a temperature of the patient's body, provided type of the treatment energy, the desired treatment effect or a comparison of one or more body parameters of the patient against previous treatment.

18. The device of claim 15, further configured to provide communication data between the device and a service;
wherein the service has authorized access to information about the device; and
wherein the communication data between the device and the service includes wear and/or consumption of the device and its components, possible optimization/actualization of a software of the device and its parts, errors in the device, or providing apps for connections to other external devices.

19. The device of claim 15, further including a security protecting the communication data.

20. A modular treatment device for improvement of a visual appearance of a patient, comprising:
a mother case including a control unit and a plurality of slots;
wherein the control unit includes a processor and a memory;
a first treatment unit and a second treatment unit removably connected to the slots of the mother case;
wherein the first and second treatment units are interconnected in the mother case; and
wherein the control unit is configured to detect and configure the first treatment unit and the second treatment unit in the mother case;
a first applicator comprising a first treatment energy source and a second treatment energy source;
wherein the first applicator is connected to the first and the second treatment units; and
wherein the first applicator is coupled to a body part of the patient;
wherein the first treatment energy source provides a first treatment energy to a body part of the patient causing a first treatment effect;
wherein the second treatment energy source provides a second treatment energy to a body part of the patient causing a second treatment effect in order to improve a visual appearance of the patient; and
wherein the second treatment energy is different than the first treatment energy.

21. The device of claim 20, wherein the first treatment energy and the second treatment energy are selected from: a radio-frequency, a plasma, an ultrasound, acoustic waves, shock waves, a light, an electric current, a magnetic field, a positive or negative pressure, a heating, or a cooling.

22. The device of claim 20, wherein the body part of the patient includes one of: a bra fat area, buttocks, saddlebags, love handles, an abdomen, hips, thighs, arms, a limb, a back, a cervical body part or a muscle or muscle group of the mentioned body parts.

23. The device of claim 20, wherein each slot comprises a connecting mechanism which is different for the first and second treatment units.

24. The device of claim 20, further comprising a second applicator including third and fourth treatment energy sources;
wherein the second applicator is connected to the first and the second treatment units; and
wherein the second applicator is coupled to the body part of the patient;
wherein the third treatment energy source provides the first treatment energy to a different body part of the patient causing the first treatment effect; and
wherein the fourth treatment energy source provides a second treatment energy to the different body part of the patient causing a second treatment effect.

25. The device of claim 20, wherein the modular treatment device is configured to provide one or more predefined treatment protocols to a user via a user interface based on a detection of the first and the second treatment units;
- wherein the control unit is configured to control the first and second treatment units; and
- wherein the modular treatment device is configured to perform a selected treatment protocol from the one or more predefined treatment protocols.

26. The device of claim 25, wherein the modular treatment device is configured to provide the first treatment energy and the second treatment energy to the body part of the patient at the same time, sequentially or with an overlay according to the selected treatment protocol.

27. The device of claim 25, wherein the treatment protocol is selected based on at least one of: a required treatment effect, age, sex, weight, height, BMI or skin type of the patient.

28. The device of claim 25, further comprising at least one sensor configured to provide feedback information to the control unit;
- wherein the at least one sensor monitors device parameters, treatment parameters or biological, physical or chemical parameters of the body part.

29. The device of claim 28, wherein the control unit is configured to adjust the selected treatment protocol based on the feedback information from the at least one sensor.

30. A modular treatment device for improvement of a visual appearance of a patient, comprising:
- a mother case comprising a control unit and a plurality of slots;
- the control unit including a processor and a memory;
- first and second treatment units removably connected to the slots of the mother case in a plug and play regime; and
- an applicator including a plurality of treatment energy sources, and configured to be connected to the first treatment unit and to the second treatment unit;
- wherein the first and second treatment units are interconnected in the mother case;
- wherein the control unit is configured to control the first and the second treatment units;
- wherein the first and the second treatment units are configured to generate a first and a second treatment energy, respectively;
- wherein the plurality of treatment energy sources comprises a first plurality of treatment energy sources and a second plurality of treatment energy sources;
- wherein the first plurality of treatment energy sources is configured to provide the first treatment energy to the body part of the patient;
- wherein the second plurality of treatment energy sources is configured to provide the second treatment energy to the body part of the patient;
- wherein the modular treatment device is configured to provide one or more predefined treatment protocols to a user via a user interface based on a detection of the first and the second treatment units; and
- wherein the modular treatment device is configured to perform a selected treatment protocol from the one or more predefined treatment protocols in order to improve the visual appearance of the patient.

31. The device of claim 30, wherein the first treatment energy is a different type of energy from the second treatment energy; and
- wherein at least one of the first or the second treatment energies is one of: a radio-frequency, a plasma, an ultrasound, acoustic waves, shock waves, a light, an electric current, a magnetic field, a positive or negative pressure, a heating, or a cooling.

32. The device of claim 31, wherein the modular treatment device is further configured to create a treatment pattern by varying intensities of the first and second treatment energies between the first and second plurality of treatment energy sources.

* * * * *